US006277989B1

(12) United States Patent
Chakravarty et al.

(10) Patent No.: US 6,277,989 B1
(45) Date of Patent: Aug. 21, 2001

(54) QUINAZOLINE DERIVATIVES AS MEDICAMENTS

(75) Inventors: Sarvajit Chakravarty, Sunnyvale, CA (US); Sundeep Dugar, Bridgewater, NJ (US); John J. Perumattam, Los Altos, CA (US); George F. Schreiner, Los Altos Hills, CA (US); David Y. Liu, Palo Alto, CA (US); John A. Lewicki, Los Gatos, CA (US)

(73) Assignee: Scios, Inc., Sunnyvale, CA (US)

( * ) Notice: Subject to any disclaimer, the term of this patent is extended or adjusted under 35 U.S.C. 154(b) by 0 days.

(21) Appl. No.: 09/525,034

(22) Filed: Mar. 14, 2000

Related U.S. Application Data

(60) Division of application No. 09/383,825, filed on Aug. 27, 1999, which is a continuation-in-part of application No. 09/141,916, filed on Aug. 28, 1998, now Pat. No. 6,184,226.

(51) Int. Cl.⁷ .................................................. C07D 239/42

(52) U.S. Cl. ........................................ 544/393; 544/284

(58) Field of Search .................................... 544/284, 293

(56) References Cited

U.S. PATENT DOCUMENTS

| 3,971,783 | * | 7/1976 | Barnish et al. | 260/256.4 |
|---|---|---|---|---|
| 4,435,003 | * | 3/1984 | Fletcher | 282/27.5 |
| 4,480,096 | * | 10/1984 | Fletcher | 544/289 |
| 4,480,220 | | 11/1984 | Young | 312/220 |
| 4,557,998 | | 12/1985 | Washburn et al. | 430/367 |
| 4,695,575 | | 9/1987 | Janssens et al. | 134/29.2 |
| 5,430,148 | | 7/1995 | Webber et al. | 544/238 |
| 5,439,895 | | 8/1995 | Lee et al. | 514/63 |
| 5,475,001 | | 12/1995 | Barker | 514/258 |
| 5,480,883 | | 1/1996 | Spada et al. | 514/249 |
| 5,616,582 | | 4/1997 | Barker | 514/234.5 |
| 5,650,410 | | 7/1997 | Sohda et al. | 514/233.8 |
| 5,658,902 | | 8/1997 | Ahn et al. | 514/234.8 |
| 5,693,652 | | 12/1997 | Takase et al. | 514/322 |
| 5,719,157 | | 2/1998 | Sohda et al. | 514/259 |
| 5,721,237 | | 2/1998 | Myers et al. | 514/259 |
| 5,801,180 | | 9/1998 | Takase et al. | 514/259 |

FOREIGN PATENT DOCUMENTS

| 893 984 | 1/1983 | (BE) . |
|---|---|---|
| 3 536 244 | 4/1986 | (DE) . |
| 3 501 696 | 7/1986 | (DE) . |
| 3 641 872 | 6/1988 | (DE) . |
| 3 909 595 | 9/1990 | (DE) . |
| 3 921 025 | 1/1991 | (DE) . |
| 4 208 254 | 9/1993 | (DE) . |
| 4 313 412 | 10/1994 | (DE) . |
| 4 313 413 | 10/1994 | (DE) . |
| 0 073 997 | 3/1983 | (EP) . |
| 0 164 204 | 12/1985 | (EP) . |
| 0 172 427 | 2/1986 | (EP) . |
| 0 242 324 | 10/1987 | (EP) . |
| 0 271 040 | 6/1988 | (EP) . |
| 0 279 681 | 8/1988 | (EP) . |
| 0 280 224 | 8/1988 | (EP) . |
| 0 283 261 | 9/1988 | (EP) . |
| 0 296 560 | 12/1988 | (EP) . |
| 0 297 661 | 1/1989 | (EP) . |
| 0 326 328 | 8/1989 | (EP) . |
| 0 326 330 | 8/1989 | (EP) . |
| 0 335 319 | 10/1989 | (EP) . |
| 0 372 998 | 6/1990 | (EP) . |
| 0 385 662 | 9/1990 | (EP) . |
| 0 385 663 | 9/1990 | (EP) . |
| 0 407 955 | 1/1991 | (EP) . |
| 0 418 071 | 3/1991 | (EP) . |
| 0 450 504 | 10/1991 | (EP) . |
| 0 462 830 | 12/1991 | (EP) . |
| 0 481 802 | 4/1992 | (EP) . |
| 0 485 290 | 5/1992 | (EP) . |
| 0567 107 | 10/1993 | (EP) . |

(List continued on next page.)

OTHER PUBLICATIONS

Lee et al. (J. Med. Chem, 38(18), 3547–3557, 1995.*
Birnbaumer et al., "Receptor–to–Effector Signaling through G Proteins: Roles for βγ Dimers as well as α Subunits," *Cell* (1992) 71:1069–1072.
Brunswick et al., "Cyclic Amidines. Part XXII. Novel Isomerism of Disubstituted Tricycloquinazolines and Molecular Orientations in Carcinogenesis," *J Chem Soc* (1970) 19:2641–2647.
Crawford et al., "Thrombospondin–1 Is a Major Activator of TGF–β1 In Vivo," *Cell* (1998) 93:1159–1170.
Dean et al., "Cyclic Amidines. Part XXI. [¹⁴C]Tricycloquinazoline and Hydroxytricyloquinazolines," *J Chem Soc* (1968) 2:142–144.

(List continued on next page.)

*Primary Examiner*—Richard L. Raymond
(74) *Attorney, Agent, or Firm*—Morrison & Foerster LLP

(57) ABSTRACT

The invention is directed to methods to inhibit TGF-β and/or p38-α kinase using compounds of the formula

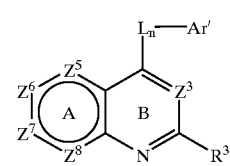

(1)

or the pharmaceutically acceptable salts thereof
  wherein $R^3$ is a noninterfering substituent;
  each Z is $CR^2$ or N, wherein no more than two Z positions in ring A are N, and wherein two adjacent Z positions in ring A cannot be N;
  each $R^2$ is independently a noninterfering substituent;
  L is a linker;
  n is 0 or 1; and
  Ar' is the residue of a cyclic aliphatic, cyclic heteroaliphatic, aromatic or heteroaromatic moiety optionally substituted with 1–3 noninterfering substituents.

6 Claims, 10 Drawing Sheets

FOREIGN PATENT DOCUMENTS

| | | |
|---|---|---|
| 0 579 263 | 1/1994 | (EP) . |
| 0 716 855 | 6/1996 | (EP) . |
| 0 742 207 | 11/1996 | (EP) . |
| 0 903 349 | 3/1999 | (EP) . |
| 2 205 118 | 11/1988 | (GB) . |
| 2 295 387 | 5/1996 | (GB) . |
| 62-165654 | 7/1987 | (JP) . |
| 62-165657 | 7/1987 | (JP) . |
| 62-166337 | 7/1987 | (JP) . |
| 62-168144 | 7/1987 | (JP) . |
| 62-168157 | 7/1987 | (JP) . |
| 62-293243 | 12/1987 | (JP) . |
| 63-41854 | 2/1988 | (JP) . |
| 63-307451 | 12/1988 | (JP) . |
| 1-106055 | 4/1989 | (JP) . |
| 1-231049 | 9/1989 | (JP) . |
| 3-240066 | 10/1991 | (JP) . |
| 3-240067 | 10/1991 | (JP) . |
| WO 83/00939 | 3/1983 | (WO) . |
| WO 83/02920 | 9/1983 | (WO) . |
| WO 91/09853 | 7/1991 | (WO) . |
| WO 92/07844 | 5/1992 | (WO) . |
| WO 92/20642 | 11/1992 | (WO) . |
| WO 92/22552 | 12/1992 | (WO) . |
| WO 93/23404 | 11/1993 | (WO) . |
| WO 96/40143 | 12/1996 | (WO) . |
| WO 97/03069 | 1/1997 | (WO) . |
| WO 97/26252 | 7/1997 | (WO) . |
| WO 98/06715 | 2/1998 | (WO) . |
| WO 98/07425 | 2/1998 | (WO) . |
| WO 98/27098 | 6/1998 | (WO) . |
| WO 98/52940 | 11/1998 | (WO) . |
| WO 99/09016 | 2/1999 | (WO) . |
| WO 99/18942 | 4/1999 | (WO) . |
| WO 99/32460 | 7/1999 | (WO) . |

OTHER PUBLICATIONS de Laszlo et al. "Pyrroles and Other Heterocycles as Inhibitors of p38 Kinase," *Bioorg Med Chem Lett* (1998) 8(19):2689–2694 (Abstract).

Eyers et al., "Conversion of SB 203580–Insensitive MAP Kinase Family Members to Drug–Sensitive Forms by a Single Amino–Acid Substitution," *Chem and Biol* (1998) 5(6):321–328.

Jiang et al., "Characterization Of The Structure And Function Of A New Mitogen–Activated Protein Kinase (p38β)," *J Biol Chem* (1996) 271(30):17920–17926.

Kumar et al., "Novel Homologues of CSBP/p38 MAP Kinase: Activation Substrate Specificity and Sensitivity to Inhibition by Pyridinyl Imidazoles," *Biochem Biophys Res Comm* (1997) 235:533–538.

Lawrence, "Transforming Growth Factor–β: a General Review," *Eur Cytokine Netw* (1996) 7(3):363–374.

Li et al., "The Primary Structure Of p38γ: A New Member Of p38 Group Of MAP Kinases," *Biochem Biophys Res Comm* (1996) 228:334–340.

Lin et al., "Expression Cloning of the TGF–β Type II Receptor, a Functional Transmembrane Serine/Threonine Kinase," *Cell* (1992) 68:775–785.

López–Casillas et al., "Structure and Expression of the Membrane Proteoglycan Betaglycan, a Component of the TGF–β Receptor System," *Cell* (1991) 67:785–795.

Lyons et al., "Transforming Growth Factors and the Regulation of Cell Proliferation" *Eur J Biochem* (1990) 187:467–473.

Manhas et al., "Heterocyclic Compounds XII. Quinazoline Derivatives as Potential Antifertility Agents (I)," *J. Heterocyclic Chem* (1979) 16(4):711–715.

Massagué, "Receptors for the TGF–β Family," *Cell* (1992) 69:1067–1070.

Massagué, "TGF–β Signal Transduction," *Ann Rev Biochem* (1998) 67:753–791.

Massagué, "The Transforming Growth Factor–β Family," *Ann Rev Cell Biol* (1990) 6:597–646.

Munger et al., "Latent Transforming Growth Factor–β: Structural Features and Mechanisms of Activation," *Kidney Intl* (1997) 51:1376–382.

Munger et al., "The Integrin αvβ6 Binds and Activates Latent TGFβ1: A Mechanism for Regulating Pulmonary Inflammation and Fibrosis," *Cell* (1999) 96:319–328.

Roberts and Sporn, Handbook of Experimental Pharmacology (1990) 95:419–458.

Stein et al., "p38–2, a Novel Mitogen–Activated Protein Kinase with Distinct Properties," *J Biol Chem* (1997) 272:19509–19517.

Wahl et al., "Inflammatory and Immunomodulatory Roles of TGF–β," *Immunol Today* (1989) 10(8):258–261.

Wang et al., "Expression Cloning and Characterization of the TGF–β Type III Receptor," *Cell* (1991) 67:797–805.

Wang et al., "Molecular Cloning and Characterization of a Novel p38 Mitogen–Activated Protein Kinase," *J Biol Chem* (1997) 272(38):23668–23674.

Wang et al., "Cardiac Muscle Cell Hypertrophy and Apoptosis Induced By Distinct Members Of the p38 Mitogen–Activated Protein Kinase Family," *J Biol Chem* (1988) 273(4):2161–2168.

Wrana et al., "TGFβ Signals through a Heterometric Protein Kinase Receptor Complex," *Cell* (1992) 71:1003–1014.

* cited by examiner

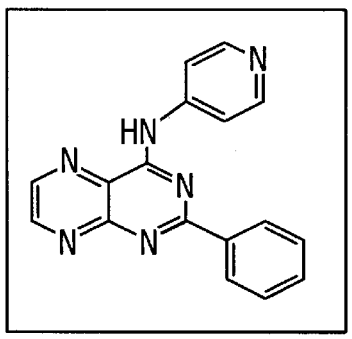
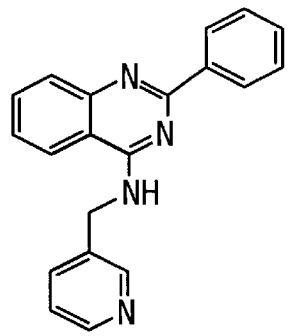
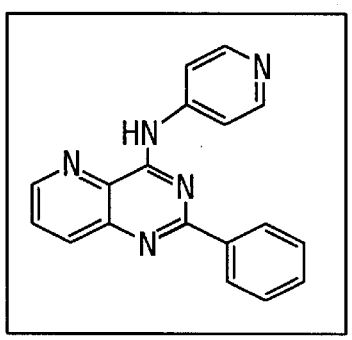
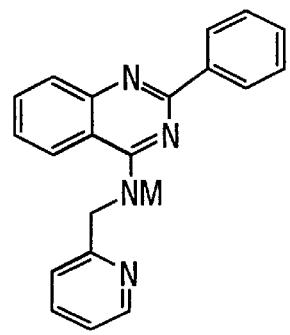
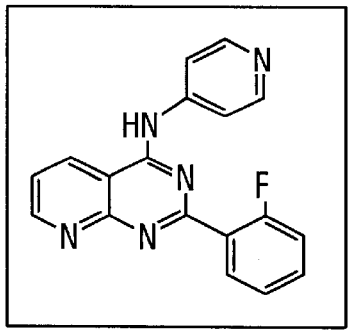
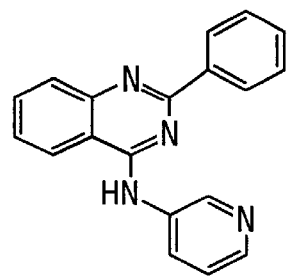
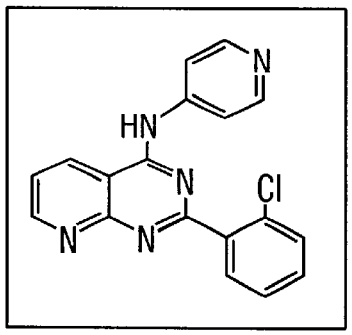
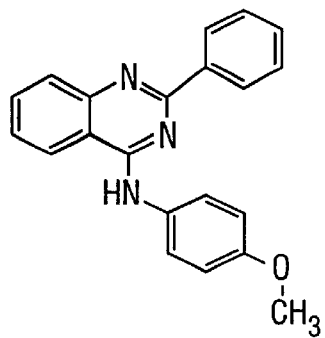
*FIG. 1A-3*
*FIG. 1B-1*

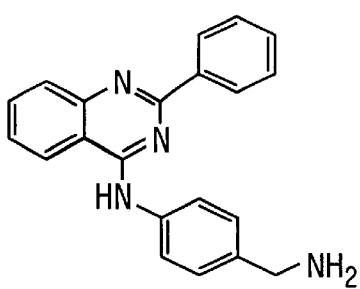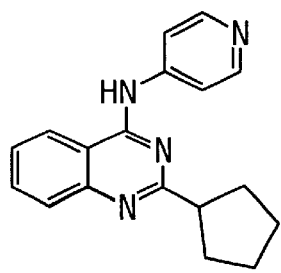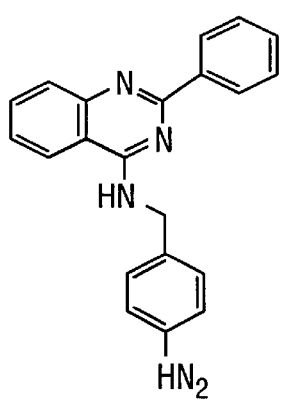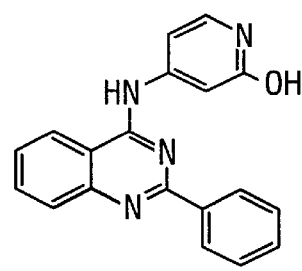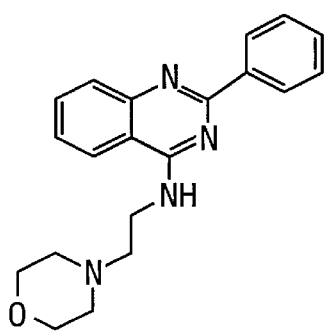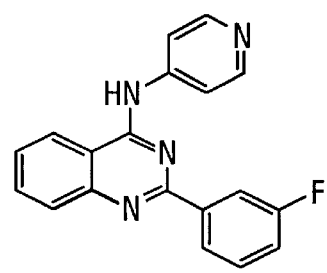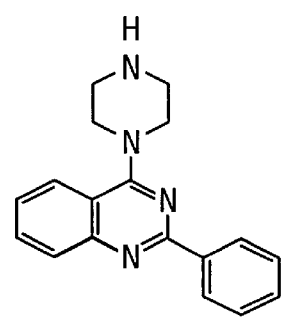
*FIG. 1B-5*
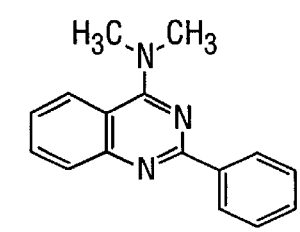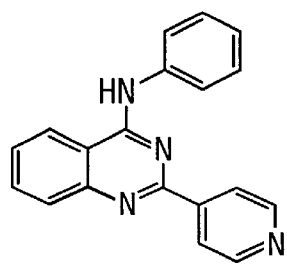
*FIG. 1C-1*

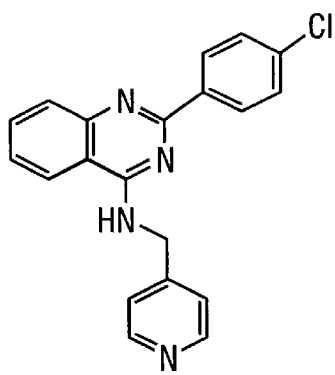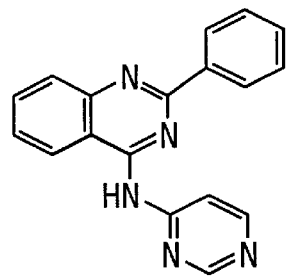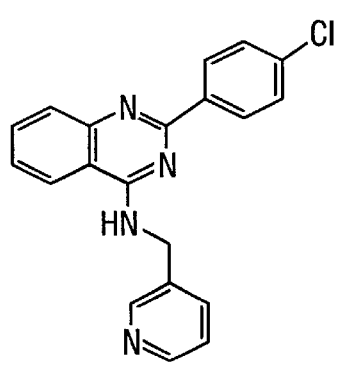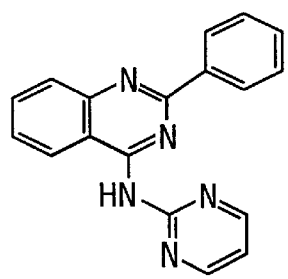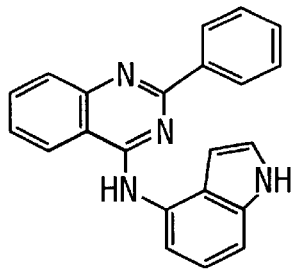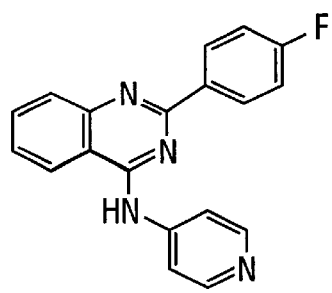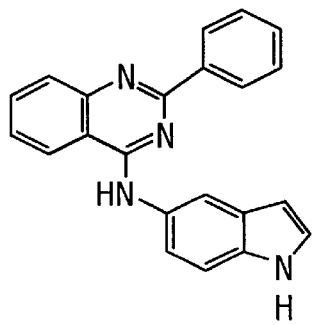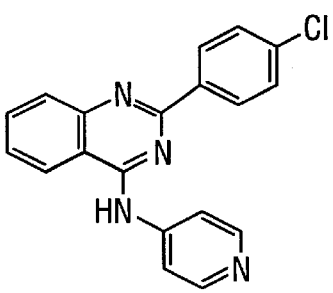
*FIG. 1C-4*

QUINAZOLINE DERIVATIVES AS MEDICAMENTS

This application is a divisional of application Ser. No. 09/383,825, filed Aug. 27, 1999, which is a continuation-in-part of Ser. No. 09/141,916, now U.S. Pat. No. 6,184,226, filed Aug. 28, 1998.

FIELD OF THE INVENTION

The invention relates to treating various disorders associated with enhanced activity of kinase p38-α and/or transforming growth factor beta (TGF-β). More specifically, it concerns compounds that are related to quinazoline as useful in these methods.

BACKGROUND ART

A large number of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful antiinflammatory agents.

Transforming growth factor-beta (TGF-β) denotes a family of proteins, TGF-β1, TGF-β2, and TGF-β3, which are pleiotropic modulators of cell growth and differentiation, embryonic and bone development, extracellular matrix formation, hematopoiesis, immune and inflammatory responses (Roberts and Sporn *Handbook of Experimental Pharmacology* (1990) 95:419–58; Massague et al. *Ann Rev Cell Biol* (1990) 6:597–646). Other members of this superfamily include activin, inhibin, bone morphogenic protein, and Mullerian inhibiting substance. TGF-β initiates an intracellular signaling pathway leading ultimately to the expression of genes that regulate the cell cycle, control proliferative responses, or relate to extracellular matrix proteins that mediate outside-in cell signaling, cell adhesion, migration and intercellular communication.

Therefore, inhibitors of the TGF-β intracellular signaling pathway are useful treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderna, dermnatomyositis, eosinophilic fasciitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis.

Eye diseases associated with a fibroproliferative condition include retinal reattachment surgery accompanying proliferative vitreoretinopathy, cataract extraction with intraocular lens implantation, and post glaucoma drainage surgery.

PCT applications WO98/06715, WO98/07425, and WO 96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3- or 4-position with a piperazine ring linked through a carboxamide linkage. Additional compounds which are conjugates of piperazines with indoles are described as insecticides in WO97/26252, also incorporated herein by reference.

The compounds of the invention are quinazoline derivatives. Other quinazoline compounds for other uses have been described. U.S. Pat. No. 5,721,237 assigned to Rhone-Poulenc Rorer is directed to methods for selective treatment of cell growth and differentiation characterized by activity of human epidermal growth factor receptor type II using quinazoline substituted only in the 4-position with an aromatic moiety optionally coupled to the quinazoline through a linking moiety. U.S. Pat. No. 4,480,883 describes compounds that exhibit tyrosine kinase inhibition activity wherein the heterocyclic portion of a quinazoline or other fused ring nitrogen-containing aromatic system is substituted only once with an aromatic moiety, again optionally coupled through a linker. U.S. Pat. No. 5,616,582 assigned to Zeneca describes tyrosine kinase inhibitors which are quinazolines linked through an amino group at the 4-position to a substituted or unsubstituted phenyl. These compounds contain no substituents at position 2. U.S. Pat. No. 5,475,001 also assigned to Zeneca describes similar compounds with the same activity. U.S. Pat. No. 5,430,148 assigned to Agouron Pharmaceutical describes antiproliferative substituted quinazolinones and their counterparts wherein the keto group is replaced by a sulfone.

U.S. Pat. No. 5,719,157 to Takeda Chemical Industries describes pharmaceutical compositions for inhibiting bone resorption which include 4-phenyl quinoline derivatives which may further be substituted at the 2-position with an optionally substituted hydrocarbon group or an optionally substituted heterocyclic group.

None of the foregoing patents describes quinazoline derivatives which specifically inhibit p38-α or TGF-β.

DISCLOSURE OF THE INVENTION

The invention is directed to methods and compounds useful in treating conditions that are characterized by enhanced p38-α activity and/or TGF-β activity. These conditions include inflammation, proliferative diseases, and certain cardiovascular disorders as further described below.

Compounds of the invention have been found to inhibit p38 kinase, the α-isoform in particular, and/or TGF-β and are thus useful in treating diseases mediated by these activities. The compounds of the invention are of the formula

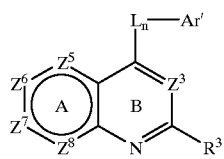

(1)

or the pharmaceutically acceptable salts thereof
wherein $R^3$ is a noninterfering substituent;
each Z is $CR^2$ or N, wherein no more than two Z positions in ring A are N, and wherein two adjacent Z positions in ring A cannot be N;
each $R^2$ is independently a noninterfering substituent;
L is a linker;
n is 0 or 1; and
Ar' is the residue of a cyclic aliphatic, cyclic heteroaliphatic, aromatic or heteroaromatic moiety optionally substituted with 1–3 noninterfering substituents.

The invention is directed to methods of treating inflammation or proliferative conditions using these compounds. The invention is also directed to treating conditions associated with cardiac failure using the invention compounds.

MODES OF CARRYING OUT THE INVENTION

Figures 1, 1A:
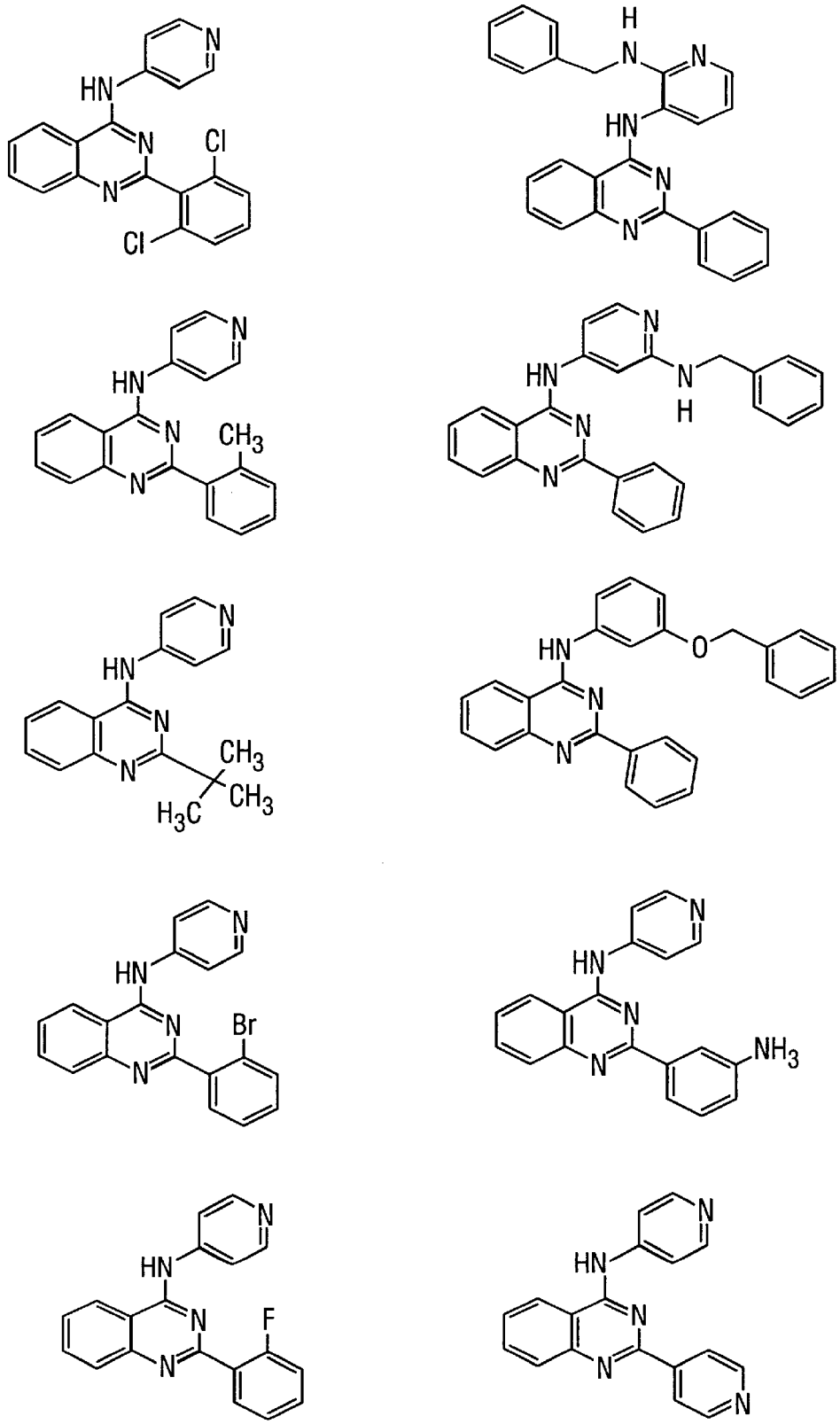
FIGS. 1A–1C show the structures of compounds prepared according to the methods of the invention and useful in the invention methods.
Figures 1, 1A, 2:
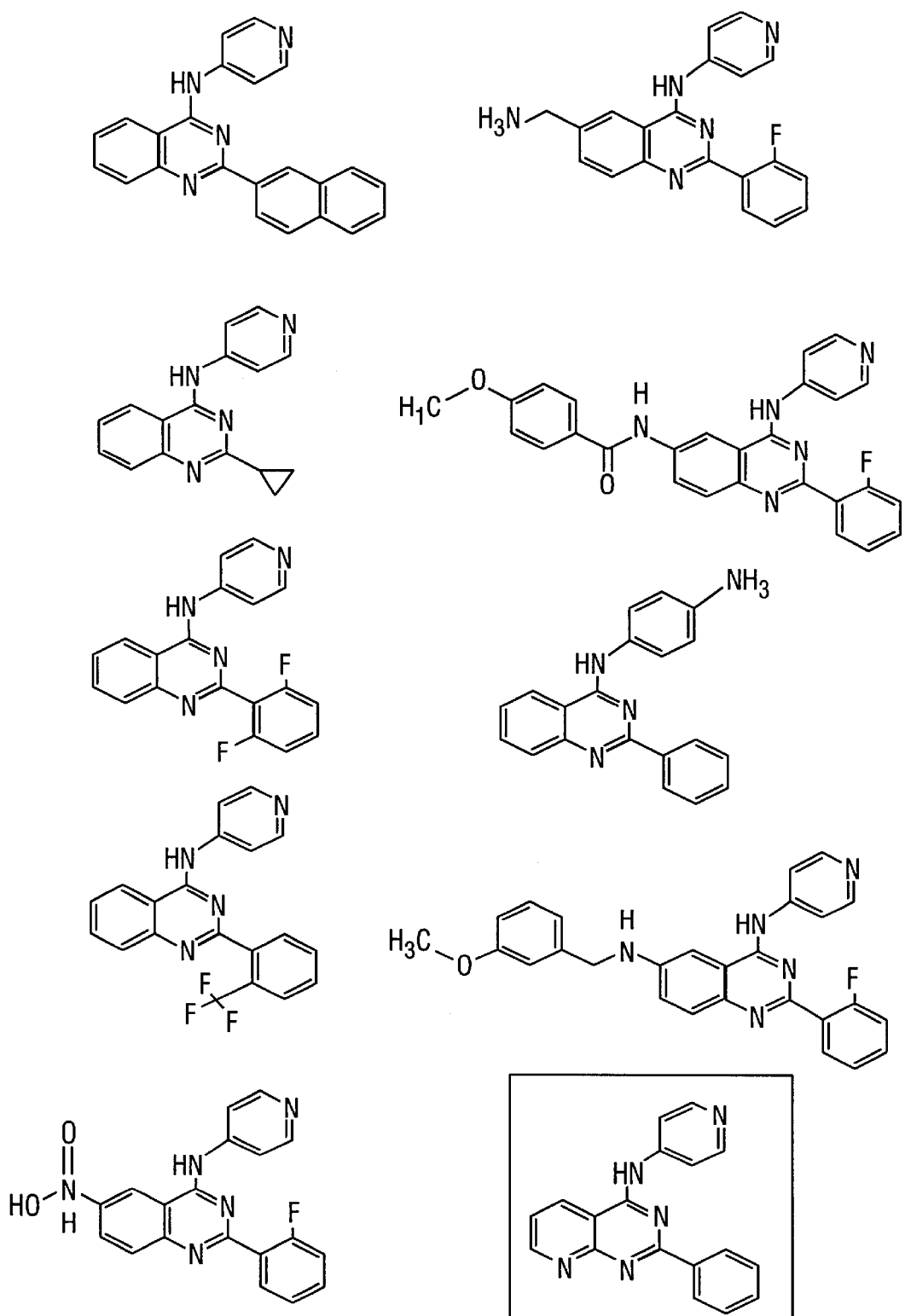

The compounds of formula (1) are useful in treating conditions which are characterized by overactivity of p38 kinase, in particular the α-isoform and/or overactivity of TGF-β. Conditions "characterized by enhanced p38-α activity" include those where this enzyme is present in increased amount or wherein the enzyme has been modified to increase its inherent activity, or both. Conditions "characterized by enhanced TGF-β activity" include those wherein TGF-β synthesis is stimulated so that TGF-β is present in enhanced amount or wherein TGF-β latent protein is undesirably activated or converted to active TGF-β protein or wherein TGF-β receptors are upregulated or wherein the TGF-β protein shows enhanced binding to cells or extracellular matrix in the location of the disease. Thus, in either case, "enhanced activity" refers to any condition wherein the effectiveness of either of these proteins is undesirably high, regardless of the cause.

The compounds of the invention are useful in conditions where either p38-α kinase or TGF-β shows enhanced activity since these compounds inhibit the activities of both proteins. This is particularly advantageous in conditions which are characterized by enhanced activities of both proteins. These conditions are those in which fibrosis and organ sclerosis are caused by, or accompanied by, inflammation, oxidation injury, hypoxia, altered temperature or extracellular osmolarity, conditions causing cellular stress, apoptosis or necrosis. These conditions include ischemia-reperfusion injury, congestive heart failure, progressive pulmonary and bronchial fibrosis, hepatitis, arthritis, inflammatory bowel disease, glomerular sclerosis, interstitial renal fibrosis, chronic scarring diseases of the eyes, bladder and reproductive tract, bone marrow dysplasia, chronic infectious or autoimmune states and traumatic or surgical wounds. These conditions, of course, would be benefited by compounds which inhibit either TGF-β or p38-α. They are especially benefited by treatment with compounds that inhibit both. Methods of treatment with the compounds of the invention are further discussed below.

The Invention Compounds

The compounds useful in the invention are derivatives of quinazoline and related compounds containing mandatory substituents at positions corresponding to the 2- and 4-positions of quinazoline. In general, a quinazoline nucleus is preferred, although alternatives within the scope of the invention are also illustrated below. Preferred embodiments for $Z^3$ are N and CH; preferred embodiments for $Z^5$–$Z^8$ are $CR^2$. However, each of $Z^5$–$Z^8$ can also be N, with the proviso noted above. Thus, with respect to the basic quinazoline type ring system, preferred embodiments include quinazoline per se, and embodiments wherein all of $Z^5$–$Z^8$ as well as $Z^3$ are either N or CH. Also preferred are those embodiments wherein $Z^3$ is N, and either $Z^5$ or $Z^8$ or both $Z^5$ and $Z^8$ are N and $Z^6$ and $Z^7$ are CH or $CR^2$. Where $R^2$ is other than H, it is preferred that $CR^2$ occur at positions 6 and/or 7.

As used herein, a "noninterfering substituent" is a substituent which leaves the ability of the compound of formula (1) to inhibit p38-α activity and/or TGF-β activity qualitatively intact. Thus, the substituent may alter the degree of inhibition and the balance between p38-α inhibition and TGF-β inhibition. However, as long as the compound of formula (1) retains the ability to inhibit either p38-α or TGF-β activity or both, the substituent will be classified as "noninterfering."

As used herein, "hydrocarbyl residue" refers to a residue which contains only carbon and hydrogen. The residue may be aliphatic or aromatic, straight-chain, cyclic, branched, saturated or unsaturated. The hydrocarbyl residue, when indicated, may contain heteroatoms over and above the carbon and hydrogen members of the substituent residue. Thus, when specifically noted as containing such heteroatoms, the hydrocarbyl residue may also contain carbonyl groups, amino groups, hydroxyl groups and the like, or contain heteroatoms within the "backbone" of the hydrocarbyl residue.

As used herein, the term "alkyl," "alkenyl" and "alkynyl" include straight- and branched-chain and cyclic monovalent substituents. Examples include methyl, ethyl, isobutyl, cyclohexyl, cyclopentylethyl, 2-propenyl, 3-butynyl, and the-like. Typically, the alkyl, alkenyl and alkynyl substituents contain 1-10C (alkyl) or 2-10C (alkenyl or alkynyl). Preferably they contain 1-6C (alkyl) or 2-6C (alkenyl or alkynyl). Heteroalkyl, heteroalkenyl and heteroalkynyl are similarly defined but may contain 1–2 O, S or N heteroatoms or combinations thereof within the backbone residue.

As used herein, "acyl" encompasses the definitions of alkyl, alkenyl, alkynyl and the related hetero-forms which are coupled to an additional residue through a carbonyl group.

"Aromatic" moiety refers to a monocyclic or fused bicyclic moiety such as phenyl or naphthyl; "heteroaromatic" also refers to monocyclic or fused bicyclic ring systems containing one ore more heteroatoms selected from O, S and N. The inclusion of a heteroatom permits inclusion of 5-membered rings as well as 6-membered rings. Thus, typical aromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Any monocyclic or fused ring bicyclic system which has the characteristics of aromaticity in terms of electron distribution throughout the ring system is included in this definition. Typically, the ring systems contain 5–12 ring member atoms.

Similarly, "arylalkyl" and "heteroalkyl" refer to aromatic and heteroaromatic systems which are coupled to another residue through a carbon chain, including substituted or unsubstituted, saturated or unsaturated, carbon chains, typically of 1-6C. These carbon chains may also include a carbonyl group, thus making them able to provide substituents as an acyl moiety.

With respect to the substituent at the positions corresponding to the 4-position of quinazoline, LAr', L is present or absent and is a linker which spaces the substituent Ar' from ring B at a distance of 2–8 Å, preferably 2–6 Å, more preferably 2–4 Å. The distance is measured from the ring carbon in ring B to which one valence of L is attached to the atom of the Ar' cyclic moiety to which the other valence of the linker is attached. The Ar' moiety may also be coupled directly to ring B (i.e., when n is 0). Typical, but nonlimiting, embodiments of L are of the formula $S(CR^2_2)_m$, —$NR^1SO_2(CR^2_2)_l$, $NR^1(CR^2_2)_m$, $NR^1CO(CR^2_2)_l$, $O(CR^2_2)_m$, $OCO(CR^2_2)_l$, and

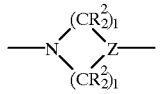

wherein Z is N or CH and wherein m is 0–4 and l is 0–3, preferably 1–3 and 1–2, respectively. L preferably provides —$NR^1$— coupled directly to ring B. A preferred embodiment of $R^1$ is H, but $R^1$ may also be acyl, alkyl, arylacyl or arylalkyl where the aryl moiety may be substituted by 1–3 groups such as alkyl, alkenyl, alkynyl, acyl, aryl, alkylaryl, aroyl, N-aryl, NH-alkylaryl, NH-aroyl, halo, OR, $NR_2$, SR, —SOR, —NRSOR, —$NRSO_2R$, —$SO_2R$, —OCOR, —NRCOR, —$NRCONR_2$, —NRCOOR, —$OCONR_2$, —RCO, —COOR, —$SO_3R$, —$CONR_2$, $SO_2NR_2$, CN, $CF_3$, and $NO_2$, wherein each R is independently H or alkyl (1-4C), preferably the substituents are alkyl (1-6C), OR, SR or $NR_2$ wherein R is H or lower alkyl (1-4C). More preferably, $R^1$ is H or alkyl (1-6C). Any aryl groups contained in the substituents may further be substituted by for example alkyl, alkenyl, alkynyl, halo, OR, $NR_2$, SR, —SOR, —$SO_2R$, —OCOR, —NRCOR, —$NRCONR_2$, —NRCOOR, —$OCONR_2$, —RCO, —COOR, $SO_2R$, NRSOR, $NRSO_2R$, —$SO_3R$, —$CONR_2$, $SO_2NR_2$, CN, $CF_3$, or $NO_2$, wherein each R is independently H or alkyl (1-4C).

Ar' is aryl, heteroaryl, including 6–5 fused heteroaryl, cycloaliphatic or cycloheteroaliphatic. Preferably Ar' is phenyl, 2-, 3- or 4-pyridyl, indolyl, 2- or 4-pyrimidyl, benzimidazolyl, indolyl, preferably each optionally substituted with a group selected from the group consisting of optionally substituted alkyl, alkenyl, alkynyl, aryl, N-aryl, NH-aroyl, halo, OR, $NR_2$, SR, —OOCR, —NROCR, RCO, —COOR, —$CONR_2$, $SO_2NR_2$, CN, $CF_3$, and $NO_2$, wherein each R is independently H or alkyl (1-4C).

Ar' is more preferably indolyl, 6-pyrimidyl, 3- or 4-pyridyl, or optionally substituted phenyl.

For embodiments wherein Ar' is optionally substituted phenyl, substituents include, without limitation, alkyl, alkenyl, alkynyl, aryl, alkylaryl, aroyl, N-aryl, NH-alkylaryl, NH-aroyl, halo, OR, $NR_2$, SR, —SOR, —$SO_2R$, —OCOR, —NRCOR, —$NRCONR_2$, —NRCOOR, —$OCONR_2$, RCO, —COOR, —$SO_3R$, —$CONR_2$, $SO_2NR_2$, CN, $CF_3$, and $NO_2$, wherein each R is independently H or alkyl (1-4C). Preferred substituents include halo, OR, SR, and $NR_2$ wherein R is H or methyl or ethyl. These substituents may occupy all five positions of the phenyl ring, preferably 1–2 positions, preferably one position. Embodiments of Ar' include substituted or unsubstituted phenyl, 2-, 3-, or 4-pyridyl, 2-, 4- or 6-pyrimidyl, indolyl, isoquinolyl, quinolyl, benzimidazolyl, benzotriazolyl, benzothiazolyl, benzofuranyl, pyridyl, thienyl, furyl, pyrrolyl, thiazolyl, oxazolyl, imidazolyl, and morpholinyl. Particularly preferred as an embodiment of Ar' is 3- or 4-pyridyl, especially 4-pyridyl in unsubstituted form.

Any of the aryl moieties, especially the phenyl moieties, may also comprise two substituents which, when taken together, form a 5–7 membered carbocyclic or heterocyclic aliphatic ring.

Thus, preferred embodiments of the substituents at the position of ring B corresponding to 4-position of the quinazoline include 2-(4-pyridyl)ethylamino; 4-pyridylamino; 3-pyridylamino; 2-pyridylamino; 4-indolylamino; 5-indolylamino; 3-methoxyanilinyl; 2-(2,5-difluorophenyl)ethylamino-, and the like.

$R^3$ is generally a hydrocarbyl residue (1-20C) containing 0–5 heteroatoms selected from O, S and N. Preferably $R^3$ is alkyl, aryl, arylalkyl, heteroalkyl, heteroaryl, or heteroarylalkyl, each unsubstituted or substituted with 1–3 substituents. The substituents are independently selected from a group that includes halo, OR, $NR_2$, SR, —SOR, —$SO_2R$, —OCOR, —NRCOR, —$NRCONR_2$, —NRCOOR, —$OCONR_2$, RCO, —COOR, —$SO_3R$, NRSOR, $NRSO_2R$, —$CONR_2$, $SO_2NR_2$, CN, $CF_3$, and $NO_2$, wherein each R is independently H or alkyl (1-4C) and with respect to any aryl or heteroaryl moiety, said group further including alkyl (1-6C) or alkenyl or alkynyl. Preferred embodiments of $R^3$ (the substituent at position corresponding to the 2-position of the quinazoline) comprise a phenyl moiety optionally substituted with 1–2 substituents preferably halo, alkyl (1-6C), OR, $NR_2$, and SR wherein R is as defined above. Thus, preferred substituents at the 2-position of the quinazoline include phenyl, 2-bromophenyl, 2-chlorophenyl, 2-fluorophenyl, 2-methylphenyl, 4-fluorophenyl and the like. Other preferred embodiments of $R^3$ comprise a cyclopentyl or cyclohexyl moiety.

As noted above, $R^2$ is a noninterfering substituent. As set forth above, a "noninterfering substituent" is one whose presence does not substantially destroy the p38-α kinase inhibiting ability and/or TGF-β inhibiting ability of the compound of formula (1).

Each $R^2$ is also independently a hydrocarbyl residue (1-20C) containing 0–5 heteroatoms selected from O, S and N. Preferably, $R^2$ is independently H, alkyl, alkenyl, alkynyl, acyl or hetero-forms thereof or is aryl, arylalkyl, heteroalkyl, heteroaryl, or heteroarylalkyl, each unsubstituted or substituted with 1–3 substituents selected independently from the group consisting of alkyl, alkenyl, alkynyl, aryl, alkylaryl, aroyl, N-aryl, NH-alkylaryl, NH-aroyl, halo, OR, $NR_2$, SR, —SOR, —$SO_2R$, —OCOR, —NRCOR, —$NRCONR_2$, —NRCOOR, NRSOR, $NRSO_2R$, —$OCONR_2$, RCO, —COOR, —$SO_3R$, NRSOR, $NRSO_2R$, —$CONR_2$, $SO_2NR_2$, CN, $CF_3$, and $NO_2$, wherein each R is independently H or alkyl (1-4C). The aryl or aroyl groups on said substituents may be further substituted by, for example, alkyl, alkenyl, alkynyl, halo, OR, $NR_2$, SR, —SOR, —$SO_2R$, —OCOR, —NRCOR, —$NRCONR_2$, —NRCOOR, —$OCONR_2$, RCO, —COOR, —$SO_3R$, —$CONR_2$, $SO_2NR_2$, CN, $CF_3$, and $NO_2$, wherein each R is independently H or alkyl (1-4C). More preferably the substituents on $R^2$ are selected from $R^4$, halo, $OR^4$, $NR^4_2$, $SR^4$, —$OCOR^4$, —$NRCOR^4$, —$COOR^4$, $R^4CO$, —$CONR^4_2$, —$SO^2NR^4_2$, CN, $CF_3$, and $NO_2$, wherein each $R^4$ is independently H, or optionally substituted alkyl (1-6C), or optionally substituted arylalkyl (7-12C) and wherein two $R^4$ or two substituents on said alkyl or arylalkyl taken together may form a fused aliphatic ring of 5–7 members.

$R_2$ may also, itself, be selected from the group consisting of halo, OR, $NR_2$, SR, —SOR, —SO$_2$R, —OCOR, —NRCOR, —NRCONR$_2$, —NRCOOR, NRSOR, NRSO$_2$R, —OCONR$_2$, RCO, —COOR, —SO$_3$R, NRSOR, NRSO$_2$R, —CONR$_2$, SO$_2$NR$_2$, CN, CF$_3$, and NO$_2$, wherein each R is independently H or alkyl (1-4C).

More preferred substituents represented by $R^2$ are those as set forth with regard to the phenyl moieties contained in Ar' or $R^3$ as set forth above. Two adjacent $CR^2$ taken together may form a carbocyclic or heterocyclic fused aliphatic ring of 5–7 atoms. Preferred $R^2$ substituents are of the formula $R^4$, —$OR^4$, $SR^4$ or $R^4NH$—, especially $R^4NH$—, wherein $R^4$ is defined as above. Particularly preferred are instances wherein $R^4$ is substituted arylalkyl.

The compounds of formula (1) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compound of formula (1), the compound may also be supplied as a salt with a pharmaceutically acceptable cation.

Synthesis of the Invention Compounds

The compounds of the invention may be synthesized from the corresponding 4-halo-2-phenyl quinazoline as described in Reaction Scheme 1; which may be obtained from the corresponding 4-hydroxyquinazoline as shown in Reaction Scheme 2. Alternatively, the compounds can be prepared using anthranylamide as a starting material and benzoylating the amino group followed by cyclization to obtain the intermediate 2-phenyl-4-hydroxy quinazoline as shown in Reaction Scheme 3. Reaction Schemes 4–6 are similar to Reaction Scheme 3 except that an appropriate pyridine or 1,4-pyrimidine nucleus, substituted with a carboxamide residue and an adjacent amino residue, is substituted for the anthranylimide. The compounds of the invention wherein $R^1$ is H can be further derivatized to comprise other embodiments of $R^1$ as shown in Reaction Scheme 7.

Reaction Scheme 1

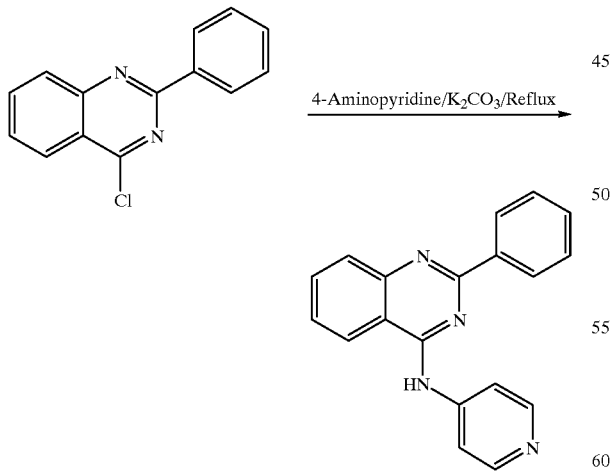

Reaction Scheme 1 is illustrative of the simple conversion of a halogenated quinazoline to compounds of the invention. Of course, the phenyl of the illustration at position 2 may be generalized as $R^3$ and the 4-pyridylamino at position 2 can be generalized to Ar'—L or Ar'—.

Reaction Scheme 2

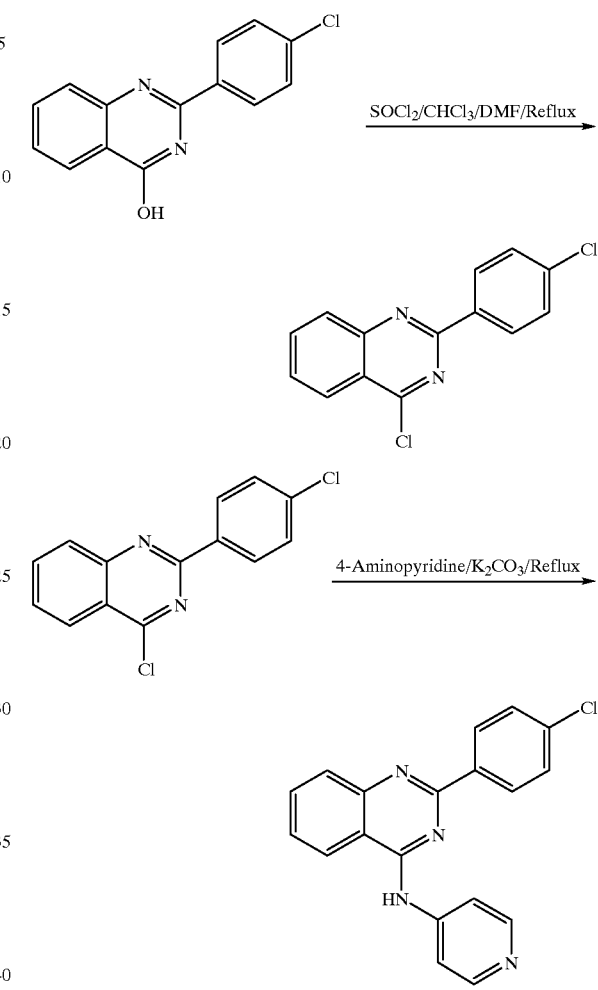

Reaction Scheme 2 can, of course, be generalized in the same manner as set forth for Reaction Scheme 1.

Reaction Scheme 3

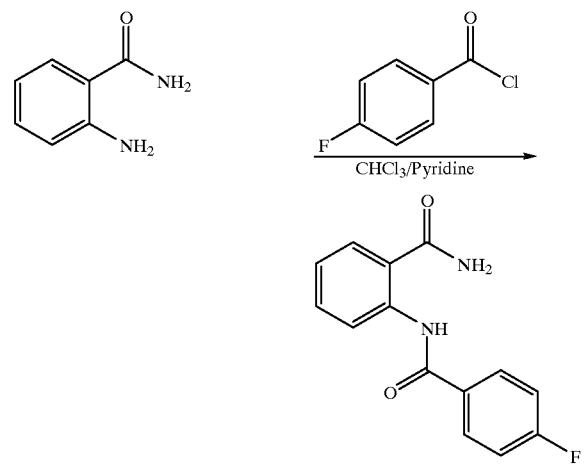

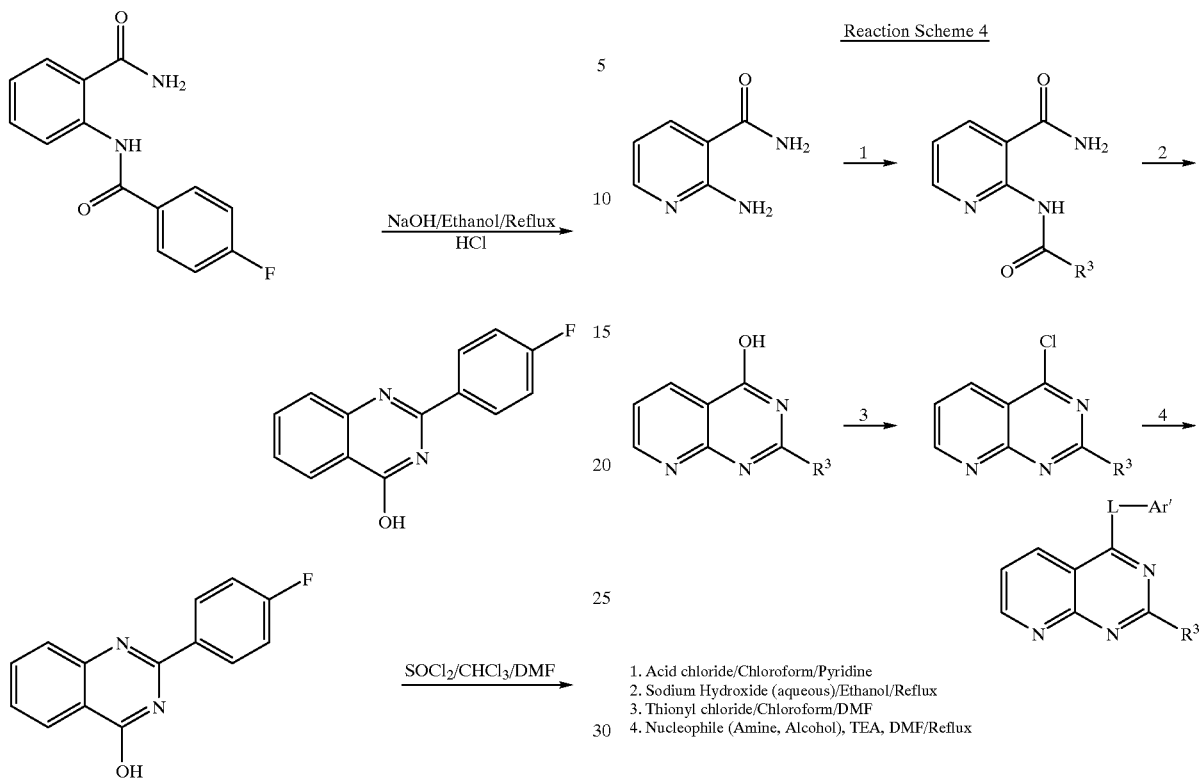
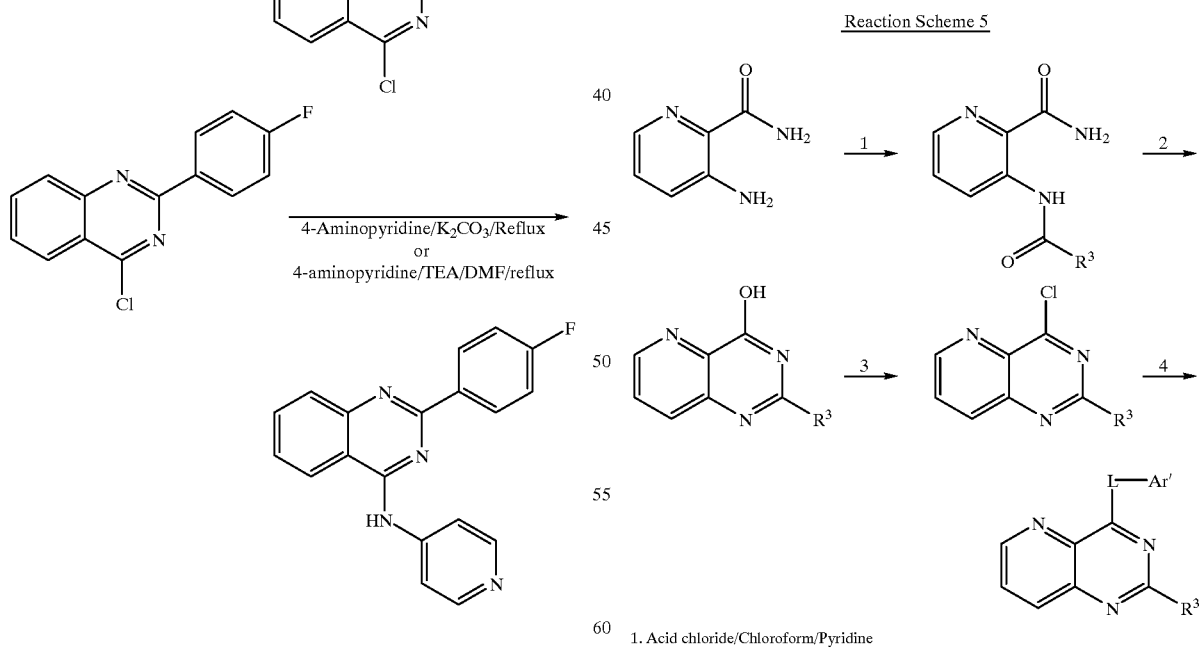
Again, Reaction Scheme 3 can be generalized by substituting the corresponding acyl halide, R³COCl for the parafluorobenzoyl chloride. Further, Ar' or Ar'—L may be substituted for 4-aminopyridine in the last step.

Reaction Scheme 6

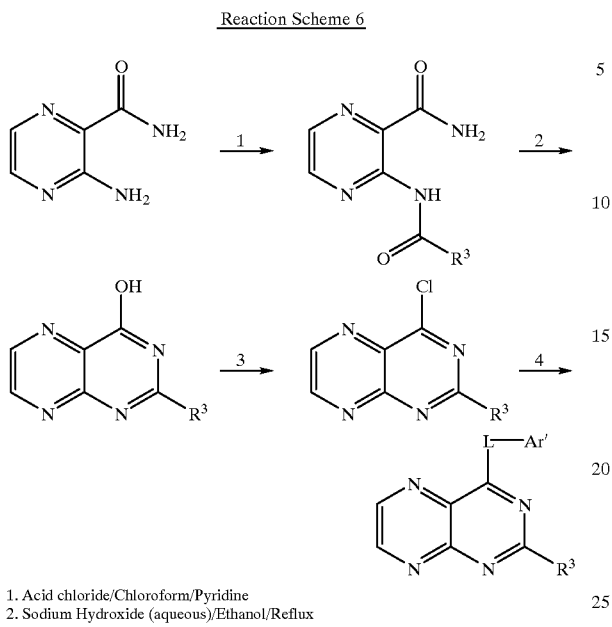

1. Acid chloride/Chloroform/Pyridine
2. Sodium Hydroxide (aqueous)/Ethanol/Reflux
3. Thionyl chloride/Chloroform/DMF
4. Nucleophile (Amine, Alcohol), TEA, DMF/Reflux It is seen that Reaction Scheme 1 represents the last step of Reaction Schemes 2–6 and that Reaction Scheme 2 represents the last two steps of Reaction Scheme 3–6.

Reaction Scheme 7 provides conditions wherein compounds of formula (1) are obtained wherein $R^1$ is other than H.

Reaction Scheme 7

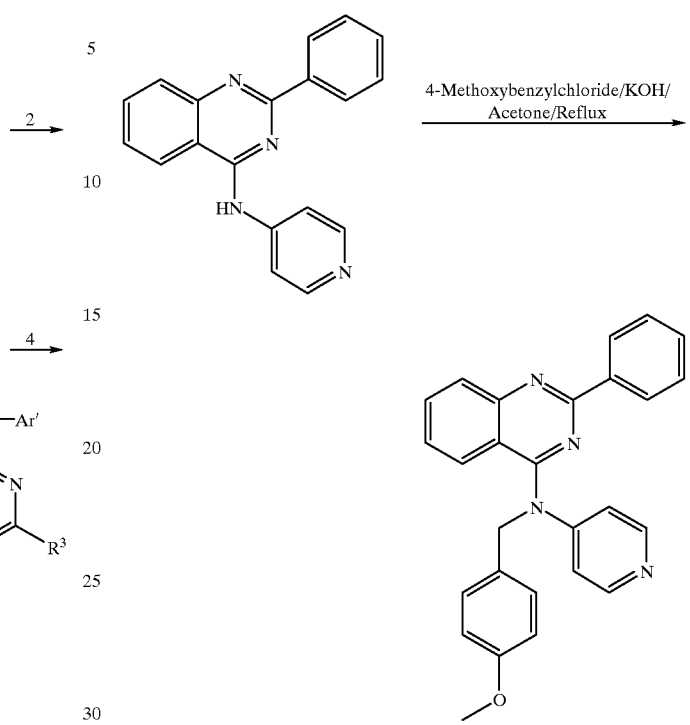

Reaction Scheme 8 is a modification of Reaction Scheme 3 which simply demonstrates that substituents on ring A are carried through the synthesis process. The principles of the behavior of the substituents apply as well to Reactions Schemes 4–6.

Reaction Scheme 8

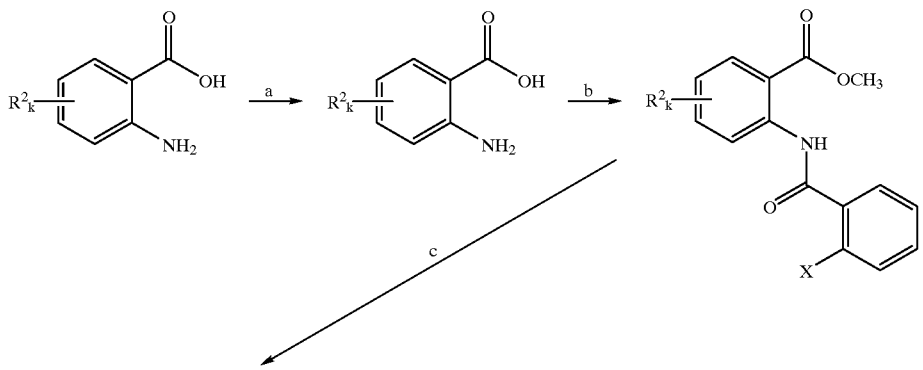

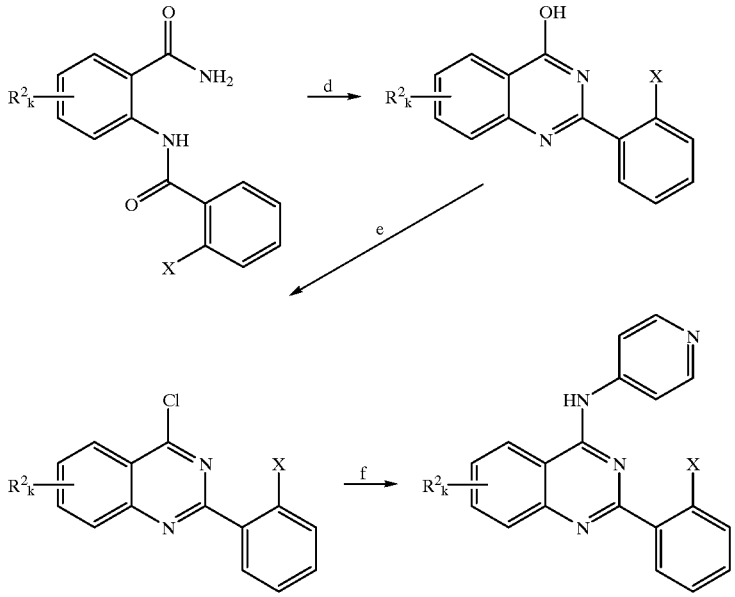

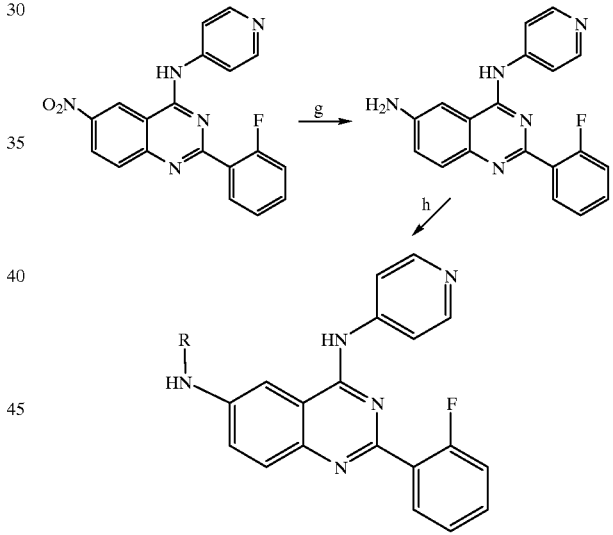

Reaction Scheme 9

Reaction Scheme 8 shows a modified form of Reaction Scheme 3 which includes substituents $R^2$ in the quinazoline ring of formula (1). The substituents are carried throughout the reaction scheme. In step a, the starting material is treated with thionyl chloride in the presence of methanol and refluxed for 12 hours. In step b, the appropriate substituted benzoyl chloride is reacted with the product of step a by treating with the appropriately substituted benzoyl chloride in pyridine for 24 hours. In embodiments wherein X (shown illustratively in the ortho-position) is fluoro, 2-fluorobenzoyl chloride is used as a reagent; where X is (for illustration ortho-chloro), 2-chlorobenzoyl chloride is used.

In step c, the ester is converted to the amide by treating in ammonium hydroxide in an aprotic solvent such as dimethyl formamide (DMF) for 24 hours. The product is then cyclized in step d by treatment with 10 N NaOH in ethanol and refluxed for 3 hours.

The resulting cyclized form is then converted to the chloride in step e by treating with thionyl chloride in chloroform in the presence of a catalytic amount of DMF under reflux for 4 hours. Finally, the illustrated 4-pyridylamino compound is obtained in step f by treating with 4-amino pyridine in the presence of potassium carbonate and DMF and refluxed for 2 hours.

In illustrative embodiments of Reaction Scheme 8, $R^2$ may, for example, provide two methoxy substituents so that the starting material is 2-amino-4,5-dimethoxy benzoic acid and the product is, for example, 2-(2-chlorophenyl)-4-(4-pyridylamino)-6,7-dimethoxyquinazoline.

In another illustrative embodiment, $R^2$ provides a single nitro; the starting material is thus, for example, 2-amino-5-nitrobenzoic acid and the resulting compound is, for example, 2(2-fluorophenyl)-4-(4-pyridylamino)-5-nitroquinazoline.

Reaction Schemes 4–6 can be carried out in a manner similar to that set forth in Reaction Scheme 8, thus carrying along $R^2$ substituents through the steps of the process.

In compounds of the invention wherein $R^2$ is nitro, the nitro group may be reduced to amino and further derivatized as indicated in Reaction Scheme 9.

In Reaction Scheme 9, the illustrative product of Reaction Scheme 8 is first reduced in step g by treating with hydrogen and palladium on carbon (10%) in the presence of acetic acid and methanol at atmospheric pressure for 12 hours to obtain the amino compound. The resulting amino compound is either converted to the acyl form (R=acyl) using the appropriate acid chloride in the presence of chloroform and pyridine for four hours, or is converted to the corresponding alkylated amine (R=alkyl) by treating the amine intermediate with the appropriate aldehyde in the presence of ethanol, acetic acid, and sodium triacetoxyborohydride for 4 hours.

While the foregoing exemplary Reaction Schemes are set forth to illustrate the synthetic methods of the invention, it is understood that the substituents shown on the quinazoline ring of the products are generically of the formula (1) as described herein and that the reactants may be substituted accordingly. Variations to accommodate various substituents which represent embodiments of $R^3$ other than the moieties shown in these illustrative examples or as Ar' in these illustrative examples may also be used. Similarly, embodiments wherein the substituent at position 4 contains an arylalkyl can be used in these schemes. Methods to synthesize the compounds of the invention are, in general, known in the art.

Administration and Use

The compounds of the invention are useful among other indications in treating conditions associated with inflammation. Thus, the compounds of formula (1) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity on such cells as cardiomyocytes, cardiofibroblasts and macrophages.

The compounds of the invention inhibit the production of cytokines such as TNF, IL-1, IL-6 and IL-8, cytokines that are important proinflammatory constituents in many different disease states and syndromes. Thus, inhibition of these cytokines has benefit in controlling and mitigating many diseases. The compounds of the invention are shown herein to inhibit a member of the MAP kinase family variously called p38 MAPK (or p38), CSBP, or SAPK-2. The activation of this protein has been shown to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as coronary artery disease, congestive heart failure, cardiomyopathy, myocarditis, vasculitis, restenosis, such as occurs following coronary angioplasty, atherosclerosis, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), silicosis, pulmonary sarcosis, sepsis, septic shock, endotoxic shock, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs host disease, bone resorption diseases like osteoporosis, type II diabetes, pyresis, psoriasis, cachexia, viral diseases such as those caused by HIV, CMV, and Herpes, and cerebral malaria.

Within the last several years, p38 has been shown to comprise a group of MAP kinases designated p38-α, p38-β, p38-γ and p38-δ. Jiang, Y. et al. *J Biol Chem* (1996) 271:17920–17926 reported characterization of p38-β as a 372-amino acid protein closely related to p38-α. In comparing the activity of p38-α with that of p38-β, the authors state that while both are activated by proinflammatory cytokines and environmental stress, p38-β was preferentially activated by MAP kinase kinase-6 (MKK6) and preferentially activated transcription factor 2, thus suggesting that separate mechanisms for action may be associated with these forms.

Kumar, S. et al. *Biochem Biophys Res Comm* (1997) 235:533–538 and Stein, B. et al. *J Biol Chem* (1997) 272:19509–19517 reported a second isoform of p38-β, p38-β2, containing 364 amino acids with 73% identity to p38-α. All of these reports show evidence that p38-β is activated by proinflammatory cytokines and environmental stress, although the second reported p38-β isoform, p38-β2, appears to be preferentially expressed in the CNS, heart and skeletal muscle compared to the more ubiquitous tissue expression of p38-α. Furthermore, activated transcription factor-2 (ATF-2) was observed to be a better substrate for p38-β2 than for p38-α, thus suggesting that separate mechanisms of action may be associated with these forms. The physiological role of p38-β1 has been called into question by the latter two reports since it cannot be found in human tissue and does not exhibit appreciable kinase activity with the substrates of p38-α.

The identification of p38-γ was reported by Li, Z. et al. *Biochem Biophys Res Comm* (1996) 228:334–340 and of p38-δ by Wang, X., et al., *J Biol Chem* (1997) 272:23668–23674 and by-Kumar, S., et al., *Biochem Biophys Res Comm* (1997) 235:533–538. The data suggest that these two p38 isoforms (γ and δ) represent a unique subset of the MAPK family based on their tissue expression patterns, substrate utilization, response to direct and indirect stimuli, and susceptibility to kinase inhibitors.

Various results with regard to response to drugs targeting the p38 family as between p38-α and either the putative p38-β1 or p38-β2 or both were reported by Jiang, Kumar, and Stein cited above as well as by Eyers, P. A. et al. *Chem and Biol* (1995) 5:321–328. An additional paper by Wang, Y. et al. *J Biol Chem* (1998) 273:2161–2168 suggests the significance of such differential effects. As pointed out by Wang, a number of stimuli, such as myocardial infarction, hypertension, valvular diseases, viral myocarditis, and dilated cardiomyopathy lead to an increase in cardiac workload and elevated mechanical stress on cardiomyocytes. These are said to lead to an adaptive hypertrophic response which, if not controlled, has decidedly negative consequences. Wang cites previous studies which have shown that in ischemia reperfusion treated hearts, p38 MAPK activities are elevated in association with hypertrophy and programmed cell death. Wang shows in the cited paper that activation of p38-β activity results in hypertrophy, whereas activation of p38-α activity leads to myocyte apoptosis. Thus, selective inhibition of p38-α activity as compared to p38-β activity will be of benefit in treating conditions associated with cardiac failure. These conditions include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the α-isoform is toxic in other muscle cell types, α-selective inhibitors would be useful for conditions associated with cachexia attributed to TNF or other conditions such as cancer, infection, or autoimmune disease.

Thus, the invention encompasses the use of compounds which selectively inhibit the activity of the p38-α isoform for treating conditions associated with activation of p38-α, in particular those associated with cardiac hypertrophy, ischemia or other environmental stress such as oxidation injury, hyperosmolarity or other agents or factors that activate p38-α kinase, or cardiac failure, for example, congestive heart failure, cardiomyopathy and myocarditis.

The TGF-β inhibition activity is useful in treating fibroproliferative diseases, treating collagen vascular disorders, treating eye diseases associated with a fibroproliferative condition, venting excessive scarring, treating neurological conditions and other conditions that are targets for TGF-β inhibitors and in preventing excessive scarring that elicits and accompanies restenosis following coronary angioplasty, cardiac fibrosis occurring after infarction and progressive heart failure, and in hypertensive vasculopathy, and keloid formation or hypertrophic scars occurring during the healing of wounds including surgical wounds and traumatic lacerations.

Neurological conditions characterized by TGF-β production include CNS injury after traumatic and hypoxic insults, Alzheimer's disease, and Parkinson's disease.

Other conditions that are potential clinical targets for TGF-β inhibitors include myelofibrosis, tissue thickening resulting from radiation treatment, nasal polyposis, polyp surgery, liver cirrhosis, and osteoporosis.

Diseases benefited by TGF-β inhibition include cardiovascular diseases such as congestive heart failure, dilated cardiomyopathy, myocarditis, or vascular stenosis associated with atherosclerosis, angioplasty treatment, or surgical incisions or mechanical trauma; kidney diseases associated with fibrosis and/or sclerosis, including glomerulonephritis of all etiologies, diabetic nephropathy, and all causes of renal interstitial fibrosis, including hypertension, complications of drug exposure, such as cyclosporin, HIV-associated nephropathy, transplant nephropathy, chronic ureteral obstruction; hepatic diseases associated with excessive scarring and progressive sclerosis, including cirrhosis due to all etiologies, disorders of the biliary tree, and hepatic dysfunction attributable to infections such as hepatitis virus or parasites; syndromes associated with pulmonary fibrosis with consequential loss of gas exchange or ability to efficiently move air into and out of the lungs, including adult respiratory distress syndrome, idiopathic pulmonary fibrosis, or pulmonary fibrosis due to infectious or toxic agents such as smoke, chemicals, allergens, or autoimmune disease; all collagen vascular disorders of a chronic or persistent nature including progressive systemic sclerosis, polymyositis, scleroderma, dermatomyositis, fascists, or Raynaud's syndrome, or arthritic conditions such as rheumatoid arthritis; eye diseases associated with fibroproliferative states, including proliferative vitreoretinopathy of any etiology or fibrosis associated with ocular surgery such as retinal reattachment, cataract extraction, or drainage procedures of any kind; excessive or hypertrophic scar formation in the dermis occurring during wound healing resulting from trauma or surgical wounds; disorders of the gastrointestinal tract associated with chronic inflammation, such as Crohn's disease or ulcerative colitis or adhesion formation as a result of trauma or surgical wounds, polyposis or states post polyp surgery; chronic scarring of the peritoneum associated with endometriosis, ovarian disease, peritoneal dialysis, or surgical wounds; neurological conditions characterized by TGF-β production or enhanced sensitivity to TGF-β, including states post-traumatic or hypoxic injury, Alzheimer's disease, and Parkinson's disease; and diseases of the joints involving scarring sufficient to impede mobility or produce pain, including states post-mechanical or surgical trauma, osteoarthritis and rheumatoid arthritis.

The modulation of the immune and inflammation systems by TGF-β (Wahl et al.

Immunol Today(1989) 10:258–61) includes stimulation of leukocyte recruitment, cytokine production, and lymphocyte effector function, and inhibition of T-cell subset proliferation, B-cell proliferation, antibody formation, and monocytic respiratory burst. TGF-β is a stimulator for the excess production of extracellular matrix proteins, including fibronectin and collagen. It also inhibits the production of enzymes that degrade these matrix proteins. The net effect is the accumulation of fibrous tissue which is the hallmark of fibroproliferative diseases.

TGF-β is active as a homodimer, but is synthesized and secreted from cells as an inactive latent complex of the mature homodimer and proregions, called latency associated protein (LAP). These proteins bind to each other through noncovalent interactions (Lyons and Moses *Eur J Biochem* (1990) 187:467). LAP is often disulfide-linked to separate gene products, called latent TGF-β binding proteins or LTBPs. These latent forms provide stability for the mature cytokine and a means for targeting it to the extracellular matrix and cell surfaces (Lawrence *Eur Cytokine Network* (1996) 7:363–74). Activation of the latent complex occurs after secretion from cells and is believed to result from the action of proteases, such as plasmin (Munger et al. *Kidney Intl* (1997) 51:1376–82), on LAP, thrombospondin-1 binding (Crawford et al. *Cell* (1998) 93:1159–70), and binding to the integrin v6 (Munger et al. *Cell* (1999) 319–28).

Other than v6 there is a variety of cell surface proteins/receptors that transduce the signals initiated by binding of the active TGF-β ligand to its receptors. These include types I, II, III, IV, and V. Type IV is present only in the pituitary gland while the others are ubiquitous. The binding affinities among the three isoforms for the type I and II receptors differ such that these two receptors bind TGF-β1 and TGF-β3 [?] more tightly than TGF-β2 (Massague Cell (1992) 69:1067–70).

The type IV receptor or endoglin has a similar isoform binding profile in contrast to the type III receptor, betaglycan, which binds equally well to all three isoforms (Wang et al. *Cell* (1991) 67:797–805; Lopez-Casillas *Cell* (1991) 67:785–95). The type V receptor binds to IGFBP-3 and is thought to have an active kinase domain similar to the type I and II receptors. Cloning of the type I and type II receptors demonstrated the existence of cytoplasmic serine/threonine kinase domains (Wrana et al. *Cell* (1992) 71:1003–14; Lin et al. *Cell* (1992) 68:775–85; Ibid. 71:1069; Massague *Cell* (1992) 69:1067–70). Initiation of the TGF-β signaling pathway results from the binding of the TGF-β ligand to the extracellular domain of the type II receptor (Massague *Ann Rev Biochem* (1998) 67:753–91). The bound receptor then recruits type I receptor into a multimeric membrane complex, whereupon the constitutively active type II receptor kinase phosphorylates and activates type I receptor kinase. The function of the type I receptor kinase is to phosphorylate a receptor-associated co-transcription factor, smad-2/3, thereby releasing it into the cytoplasm where it binds to smad-4. This smad complex translocates into the nucleus, associates with a DNA-binding cofactor, such as Fast-1, binds to enhancer regions of specific genes, and activates transcription. The expression of these genes leads to the synthesis of cell cycle regulators that control proliferative responses or extracellular matrix proteins that mediate outside-in cell signaling, cell adhesion, migration, and intercellular communication.

The manner of administration and formulation of the compounds useful in the invention and their related compounds will depend on the nature of the condition, the severity of the condition, the particular subject to be treated, and the judgement of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences,* latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

It should be noted that the compounds of formula (1) can be administered as individual active ingredients, or as mixtures of several embodiments of this formula. In addition, the inhibitors of p38 kinase or TGF-β, and dual inhibitors of p38kinase and TGF-β kinase, can be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

As implicated above, although the compounds of the invention may be used in humans, they are also available for veterinary use in treating animal subjects.

The following examples are intended to illustrate but not to limit the invention.

EXAMPLE 1

Synthesis of 4-(4-pyridylamino)-2-phenyl Quinazoline

This example illustrates Reaction Scheme 1.

A. 4-Chloro-2-phenyl quinazoline, 1 equivalent, was treated with 1 equivalent 4-aminopyridine and 1 equivalent potassium carbonate in dimethylformamide (DMF), under reflux for 4 hours. The reaction mixture was cooled to room temperature and concentrated under vacuum to an oil. This crude material was dissolved in ethyl acetate and chromatographed using hexane:ethyl acetate:methanol 8:2:0.5 to obtain solid product. Electron impact mass spectroscopy (EIMS) gave a molecular ion corresponding to the calculated molecular weight of the title compound.

B. Using the procedure of paragraph A of the example but substituting the starting materials shown in Table 1 below for 4-aminopyridine, the corresponding quinazolines shown in the table were obtained.

TABLE 1

| Substitute for 4-amino pyridine | Product obtained |
| --- | --- |
| 3-amino pyridine | 2-phenyl-4-(3-pyridylamino)-quinazoline |
| 2-amino pyridine | 2-phenyl-4-(2-pyridylamino)-quinazoline |
| 4-aminomethyl pyridine | 2-phenyl-4-(2-(4-pyridyl)methylamino)-quinazoline |
| 3-aminomethyl pyridine | 2-phenyl-4-(2-(3-pyridyl)methylamino)-quinazoline |
| 2-aminomethyl pyridine | 2-phenyl-4-(2-(2-pyridyl)methylamino)-quinazoline |

EXAMPLE 2

Synthesis of 4-(4-pyridylamino)-2-(4-chlorophenyl) Quinazoline

This example illustrates Reaction Scheme 2.

A. 4-Chloro-2-(4-chlorophenyl) quinazoline: 4-hydroxy-2-(4-chlorophenyl) quinazoline, 1 equivalent, was suspended in chloroform and treated with 12 equivalents of thionyl chloride in the presence of a catalytic amount of dimethyl formamide, under reflux for 4 hours. After removal of the solvents under reduced pressure, a solid was obtained that was analyzed by thin layer chromatography and EIMS and found to be 4-chloro-2-(4-chlorophenyl) quinazoline.

B. 4-(4-pyridylamino)-2-(4-chlorophenyl) quinazoline: 4-chloro-2-(4-chlorophenyl) quinazoline, 1 equivalent, was treated with 1 equivalent 4-aminopyridine and 1 equivalent potassium carbonate in dimethylformamide (DMF), under reflux for 4 hours, as described in Example 1. The reaction mixture was worked up as in Example 1 and product confirmed by EIMS.

EXAMPLE 3

Synthesis of 4-(4-pyridylamino)-2-(4-fluorophenyl) Quinazoline

This example illustrates Reaction Scheme 3.

A. 4-Fluorobenzoyl anthranilamide: Anthranilamide, 1 equivalent, was dissolved in chloroform/pyridine (1:1) and treated with 4-fluorobenzoyl chloride, 1.1 equivalent for one hour at room temperature. The reaction was concentrated under vacuum. The residue was taken up in ethyl acetate and washed with 1 N aqueous sodium carbonate, 10% aqueous hydrochloric acid, saturated sodium chloride solution and dried over anhydrous sodium sulfate. Concentration of the ethyl acetate layer gave a white solid that was found to be homogenous by thin layer chromatography (TLC) and confirmed by EIMS.

B. 4-Hydroxy-2-(4-fluorophenyl) quinazoline: 4-fluorobenzoyl anthranilamide, from paragraph A, 1 equivalent, was dissolved in ethanol and to this was added 10 N aqueous sodium hydroxide, 3.0 equivalents, and the resulting solution heated under reflux for 3 hours. The reaction mixture was cooled to room temperature and concentrated under vacuum. The residue was dissolved in an excess of water and acidified with concentrated hydrochloric acid. A white precipitate forms upon acidification. This precipitate was filtered and washed extensively with water. The solid was then dried under high vacuum in the presence of dessicant. The solid was found to be homogenous by TLC and product confirmed by EIMS.

C. 4-Chloro-2-(4-fluorophenyl) quinazoline: 4-hydroxy-2-(4-fluorophenyl) quinazoline, from paragraph B, 1 equivalent, was suspended in chloroform and treated with 12 equivalents of thionyl chloride in the presence of a catalytic amount of dimethyl formamide, under reflux for 4 hours. After removal of the solvents under reduced pressure a solid was obtained that was analyzed by TLC. EIMS confirmed the desired product.

D. 4-(4-pyridylamino)-2-(4-fluorophenyl) quinazoline: 4-chloro-2-(4-fluorophenyl) quinazoline from paragraph C was reacted as in Example 1 to obtain the title compound.

EXAMPLE 4

Synthesis of 2-Phenyl-4-(3-methoxyanilinyl) Quinazoline

4-Chloro-2-phenylquinazoline, 2 equivalents, 3-methoxyanilinyl, 2 equivalents, and potassium carbonate, 2 equivalents, were dissolved in 10 mL isopropanol and refluxed for 2 hours. The precipitated product formed was filtered and washed with water. Recrystallization from methanol provided the product as a white solid that was found to be homogenous by thin layer chromatography (TLC) and confirmed by EIMS.

EXAMPLE 5

Synthesis of 4-(4-Methoxybenzyl-4pyridylamino)-2-phenyl) Quinazoline 4-(4-pyridylamino)-2-phenyl quinazoline, 1 equivalent, was dissolved in reagent grade acetone, to this was added 5 equivalents of potassium hydroxide and 1.5 equivalents of 4-methoxybenzyl chloride. The mixture was refluxed under nitrogen for 4 hours. After cooling to room temperature the reaction mixture was concentrated and the residue taken up in ethyl acetate and washed with saturated aqueous sodium chloride and dried over anhydrous sodium sulfate and concentrated to give an oil. This crude material was dissolved in ethyl acetate and chromatographed as in Example 1. EIMS confirmed the product.

EXAMPLE 6

Prepared Compounds of the Invention

The compounds in Table 2 shown below have been prepared using the reaction schemes and exemplary procedures set forth herein. In the compounds of Table 2, $Z^5$–$Z^8$ are CH and $Z^3$ is N; i.e., these are all quinazoline derivatives per se. The table thus lists the embodiments of L, Ar and $R^3$.

TABLE 2

| Compound No. | L | Ar' | $R^3$ |
|---|---|---|---|
| 1 | NH | 4-pyridyl | 2-chlorophenyl |
| 2 | NH | 4-pyridyl | 2,6-dichlorophenyl |
| 3 | NH | 4-pyridyl | 2-methylphenyl |
| 4 | NH | 4-pyridyl | 2-bromophenyl |
| 5 | NH | 4-pyridyl | 2-fluorophenyl |
| 6 | NH | 4-pyridyl | 2,6-difluorophenyl |
| 7 | NH | 4-pyridyl | phenyl |
| 8 | NH | 4-pyridyl | 4-fluorophenyl |
| 9 | NH | 4-pyridyl | 4-methoxyphenyl |
| 10 | NH | 4-pyridyl | 3-fluorophenyl |
| 11* | N* | 4-pyridyl | phenyl |
| 12† | N† | 4-pyridyl | phenyl |
| 13 | NHCH$_2$ | 4-pyridyl | phenyl |
| 14 | NHCH$_2$ | 4-pyridyl | 4-chlorophenyl |
| 15 | NH | 3-pyridyl | phenyl |
| 16 | NHCH$_2$ | 2-pyridyl | phenyl |
| 17 | NHCH$_2$ | 3-pyridyl | phenyl |
| 18 | NHCH$_2$ | 2-pyridyl | phenyl |
| 19 | NHCH$_2$CH$_2$ | 2-pyridyl | phenyl |
| 20 | NH | 6-pyrimidinyl | phenyl |
| 21 | NH | 2-pyrimidinyl | phenyl |
| 22 | NH | phenyl | phenyl |
| 23 | NHCH$_2$ | phenyl | 3-chlorophenyl |
| 24 | NH | 3-hydroxyphenyl | phenyl |
| 25 | NH | 2-hydroxyphenyl | phenyl |
| 26 | NH | 4-hydroxyphenyl | phenyl |
| 27 | NH | 4-indolyl | phenyl |
| 28 | NH | 5-indolyl | phenyl |
| 29 | NH | 4-methoxyphenyl | phenyl |
| 30 | NH | 3-methoxyphenyl | phenyl |
| 31 | NH | 2-methoxyphenyl | phenyl |
| 32 | NH | 4-(2-hydroxyethyl)phenyl | phenyl |
| 33 | NH | 3-cyanophenyl | phenyl |
| 34 | NHCH$_2$ | 2,5-difluorophenyl | phenyl |
| 35 | NH | 4-(2-butyl)phenyl | phenyl |
| 36 | NHCH$_2$ | 4-dimethylaminophenyl | phenyl |
| 37 | NH | 4-pyridyl | cyclopentyl |
| 38 | NH | 2-pyridyl | phenyl |

TABLE 2-continued

| Compound No. | L | Ar' | R³ |
|---|---|---|---|
| 39 | NHCH₂ | 3-pyridyl | phenyl |
| 40 | NH | 4-pyrimidyl | phenyl |
| 41‡ | N‡ | 4-pyridyl | phenyl |
| 42 | NH | p-aminomethylphenyl | phenyl |
| 43 | NHCH₂ | 4-aminophenyl | phenyl |
| 44 | NH | 4-pyridyl | 3-chlorophenyl |
| 45 | NH | phenyl | 4-pyridyl |
| 46 | NH | 3-methyl-1H-pyrazol-5-yl | phenyl |
| 47 | NH | 4-pyridyl | t-butyl |
| 48 | NH | 2-benzylamino-3-pyridyl | phenyl |
| 49 | NH | 2-benzylamino-4-pyridyl | phenyl |
| 50 | NH | 3-benzyloxyphenyl | phenyl |
| 51 | NH | 4-pyridyl | 3-aminophenyl |
| 52 | NH | 4-pyridyl | 4-pyridyl |
| 53 | NH | 4-pyridyl | 2-naphthyl |
| 54 | 4-(CH₂)-piperidin-1-yl | 4-pyridyl | phenyl |
| 55 | 4-(CH₂)-piperazin-1-yl | phenyl | phenyl |
| 56 | piperazin-1-yl | 2-pyridyl | phenyl |
| 57 | NHCH₂CH₂ | morpholin-4-yl | phenyl |
| 58 | not present | 4-(CONH₂)-piperidin-1-yl | phenyl |
| 59 | not present | piperazin-1-yl | phenyl |
| 60 | NH | 4-pyridyl | cyclopropyl |
| 61 | NH | 4-pyridyl | 2-trifluoromethyl phenyl |
| 62 | NH | 4-aminophenyl | phenyl |
| 63 | NH | 4-pyridyl | cyclohexyl |
| 64 | NH | 3-methoxyphenyl | 2-fluorophenyl |
| 65 | NH | 4-methoxyphenyl | 2-fluorophenyl |
| 66 | NH | 4-pyrimidinyl | 2-fluorophenyl |
| 67 | NH | 3-amino-4-pyridyl | phenyl |
| 68 | NH | 4-pyridyl | 2-benzylaminophenyl |
| 69 | NH | 2-benzylaminophenyl | phenyl |
| 70 | NH | 2-benzylaminophenyl | 4-cyanophenyl |
| 71 | NH | 3'-cyano-2-benzylaminophenyl | phenyl |

\*R¹ = 2-propyl
†R¹ = 4-methoxyphenyl
‡R¹ = 4-methoxybenzyl

Compounds 1–37 in Table 2 have been assessed in terms of percent inhibition of p38-α activity in the presence of 15 μM concentration (See Example 7). The percent inhibition for all of these compounds is measurable, and is, for some compounds, as high as 100%.

The compounds in Table 3 contain modifications of the quinazoline nucleus as shown. These compounds have been prepared and tested for their ability to inhibit TGF-β and/or p38-α kinase. All of the compounds in Table 3 are embodiments of formula (1) wherein $Z^3$ is N and $Z^6$ and $Z^7$ represent CH. In all cases the linker, L, is present and is NH.

TABLE 3

| Compound No. | $Z^5$ | $Z^8$ | Ar' | $R^3$ |
|---|---|---|---|---|
| 72 | CH | N | 4-pyridyl | 2-fluorophenyl |
| 73 | CH | N | 4-pyridyl | 2-chlorophenyl |
| 74 | CH | N | 4-pyridyl | phenyl |
| 75 | N | N | 4-pyridyl | phenyl |
| 76 | N | CH | 4-pyridyl | phenyl |

Additional compounds were prepared wherein ring A contains $CR^2$ at $Z^6$ or $Z^7$ where $R^2$ is not H. These compounds, which are all quinazoline derivatives, wherein L is NH and Ar' is 4-pyridyl, are shown in Table 4. In Table 4, the percent inhibition was measured at 15 μM compound (or at 1 μM compound as indicated). See Example 7. Inhibitions above 90% were observed.

TABLE 4

| Compound No. | $R^3$ | $CR^2$ as noted |
|---|---|---|
| 77 | 2-chlorophenyl | 6,7-dimethoxy |
| 78 | 2-fluorophenyl | 6-nitro |
| 79 | 2-fluorophenyl | 6-amino |
| 80** | 2-fluorophenyl | 7-amino |
| 81** | 2-fluorophenyl | 6-(3-methoxybenzylamino) |
| 82** | 2-fluorophenyl | 6-(4-methoxybenzylamino) |
| 83 | 2-fluorophenyl | 6-(2-isobutylamino) |
| 84 | 2-fluorophenyl | 6-(4-methylmercaptobenzylamino) |
| 85 | 2-fluorophenyl | 6-(4-methoxybenzoyl amino) |
| 86 | 4-fluorophenyl | 7-amino |
| 87 | 4-fluorophenyl | 7-(3-methoxybenzylamino) |

**Tested at 1 μM

EXAMPLE 7

Assay for p38 Kinase Inhibition

The compounds to be tested were solubilized in DMSO and diluted into water to the desired concentrations. The p38 kinase was diluted to 10 μg/ml into a buffer containing 20 mM MOPS, pH 7.0, 25 mM beta-glycerol phosphate, 2 mg/ml gelatin, 0.5 mM EGTA, and 4 mM DTT.

The reaction was carried out by mixing 20 μl test compound with 10 μl of a substrate cocktail containing 500 μg/ml peptide substrate and 0.2 mM ATP (+200 μCi/ml gamma-32P-ATP) in a 4× assay buffer. The reaction was initiated by the addition of 10 μl of p38 kinase. Final assay conditions were 25 mM MOPS, pH 7.0, 26.25 mM beta-glycerol phosphate, 80 mM KCl, 22 mM $MgCl_2$, 3 mM $MgSO_4$, 1 mg/ml gelatin, 0.625 mM EGTA, 1 mM DTT, 125 μg/ml peptide substrate, 50 μM ATP, and 2.5 μg/ml enzyme. After a 40 minute incubation at room temperature, the reaction was stopped by the addition of 10 μl per reaction of 0.25 M phosphoric acid.

A portion of the reaction was spotted onto a disk of P81 phosphocellulose paper, the filters were dried for 2 minutes and then washed 4× in 75 mM $H_3PO_4$. The filters were rinsed briefly in 95% ethanol, dried, then placed in scintillation vials with liquid scintillation cocktail.

Alternatively, the substrate is previously biotinylated and the resulting reactions are spotted on SAM$^{2TM}$ streptavidin filter squares (Promega). The filters are washed 4× in 2M NaCl, 4× in 2M NaCl with 1% phosphoric acid, 2× in water, and briefly in 95% ethanol. The filter squares are dried and placed in scintillation vials with liquid scintillation cocktail.

Counts incorporated are determined on a scintillation counter. Relative enzyme activity is calculated by subtracting background counts (counts measured in the absence of enzyme) from each result, and comparing the resulting counts to those obtained in the absence of inhibitor.

$IC_{50}$ values were determined with curve-fitting plots available with common software packages. Approximate $IC_{50}$ values were calculated using formula $$IC_{50}(app) = A \times i/(1-A)$$

where A=fractional activity and i=total inhibitor concentration.

The compounds in Table 5 have $IC_{50}$ in the range of 0.1–1.5 μM vs p38-α:

TABLE 5

| Compound No. | Compound Name |
|---|---|
| 16 | 2-phenyl-4-(4-pyridylmethylamino)-quinazoline |
| 7 | 2-phenyl-4-(4-pyridylamino)-quinazoline |
| 8 | 2-(4-fluorophenyl)-(4-pyridylamino)-quinazoline |
| 1 | 2-(2-chlorophenyl)-(4-pyridylamino)-quinazoline |
| 30 | 2-phenyl-4-(3-methoxyanilinyl)-quinazoline |
| 5 | 2-(2-fluorophenyl)-4-(4-pyridylamino)-quinazoline |
| 4 | 2-(2-bromophenyl)-4-(4-pyridylamino)-quinazoline |
| 3 | 2-(2-methylphenyl)-4-(4-pyridylamino)-quinazoline |
| 79 | 2-(2-fluorophenyl)-4-(4-pyridylamino)-6-amino quinazoline |

Compounds 5 and 7 were tested for their specificity for p38 by assessing their ability to inhibit other kinases. These compounds were tested at 50 μM and were soluble at 250 μM in 5% DMSO/95% water. The results are shown in Table 6.

TABLE 6

$IC_{50}$ (app) - μM

| Compound | p38-γ | JNK1 | PKA | PKC | DNA-dep PK (PKD) | cck2 | EGF-R |
|---|---|---|---|---|---|---|---|
| 5 | 227 | 167 | >250 | >100 | 120 | 245 | 4.2 |
| 7 | >300 | >300 | 310 | >500 | 240 | >500 | 34 |

In Table 6, compound 5 is 2-(2-fluorophenyl)-4-(4-pyridylamino)-quinazoline and compound 7 is 2-phenyl-4-(4-pyridylamino)-quinazoline.

As seen in Table 6, these compounds are highly specific for p38-α. In addition, these compounds were assessed with respect to p38-β and gave curve fitted values of $IC_{50}$ as follows: Compound 5: 0.928 μM; Compound 7: 3.65 μM.

What is claimed is:

1. A compound of the formula

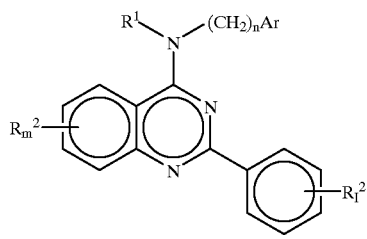

and the pharmaceutically acceptable salts thereof, wherein $R^1$ is H, alkyl (1-6C) or arylalkyl optionally substituted on the aryl group with 1–3 substituents independently selected from alkyl (1-6C), halo, OR, $NR_2$, SR, —OOCR, —NROCR, RCO, —COOR, —$CONR_2$, —$SO_2NR_2$, CN, $CF_3$, and $NO_2$, wherein each R is independently H or lower alkyl (1-4C);

each $R^2$ is independently alkyl (1-6C), halo, OR, SR, OOCR, NROCR, COOR, RCO, $CONR_2$, $SO_2NR_2$, CN, $CF_3$ or $NO_2$, wherein each R is independently H or lower alkyl (1-4C);

each of l, m, and n is independently 0, 1 or 2; and

Ar is phenyl, 2-, 3- or 4-pyridyl, indolyl, 2- or 4-pyrimidyl, or benzimidazolyl, each optionally substituted with optionally substituted alkyl, alkenyl, alkynyl, aryl, N-aryl, NH-aroyl, halo, OR, $NR_2$, SR, —OOCR, —NROCR, RCO, —COOR, —$CONR_2$, $SO_2NR_2$, CN, $CF_3$, or $NO_2$, wherein each R is independently H or alkyl (1-4C);

with the proviso that if l is 0, Ar must be optionally substituted 4-pyridyl, indolyl, 2- or 4-pyrimidyl, or benzimidazolyl.

2. The compound of claim 1 wherein $R^2$ is halo, m is 0, and l is 1 or 2.

3. The compound of claim 1 wherein Ar is 4-pyridyl.

4. The compound of claim 1 wherein $R^1$ is H.

5. The compound of claim 1 wherein $R^2$ is halo and l is 1 or 2 and m is 1 or 2.

6. A compound selected from the group consisting of
2-phenyl-4-(4-pyridylamino)-quinazoline;
2-(2-bromophenyl)-4-(4-pyridylamino)-quinazoline;
2-(2-chlorophenyl)-4-(4-pyridylamino)-quinazoline;
2-(2-fluorophenyl)-4-(4-pyridylamino)-quinazoline;
2-(2-methylphenyl)-4-(4-pyridylamino)-quinazoline;
2-(4-fluorophenyl)-4-(4-pyridylamino)-quinazoline;
2-(3-methoxyanilyl)-4-(4-pyridylamino)-quinazoline;
2-(2,6-dichlorophenyl)-4-(4-pyridylamino)-quinazoline;
2-(2,6-dibromophenyl)-4-(4-pyridylamino)-quinazoline;
2-(2,6-difluorophenyl)-4-(4-pyridylamino)-quinazoline;
2-(2-fluorophenyl)-4-(4-pyridylamino)-6,7-dimethoxyquinazoline;
2-(4-fluorophenyl)-4-(4-pyridylamino)-6,7-dimethoxyquinazoline;
2-(2-fluorophenyl)-4-(4-pyridylamino)-6-nitroquinazoline;
2-(2-fluorophenyl)-4-(4-pyridylamino-6-aminoquinazoline;
2-(2-fluorophenyl)-4-(4-pyridylamino)-7-aminoquinazoline;
2-(2-fluorophenyl)-4-(4-pyridylamino)-6-(3-methoxybenzylamino)-quinazoline;
2-(2-fluorophenyl)-4-(4-pyridylamino)-6-(4-methoxybenzylamino)-quinazoline;
2-(2-fluorophenyl)-4-(4-pyridylamino)-6-(2-isobutylamino)-quinazoline; and
2-(2-fluorophenyl)-4-(4-pyridylamino)-6-(4-methylmercaptobenzylamino)-quinazoline; and
the pharmaceutically acceptable salts thereof.

* * * * *

UNITED STATES PATENT AND TRADEMARK OFFICE
CERTIFICATE OF CORRECTION

PATENT NO. : 6,277,989 B1
DATED : August 21, 2001
INVENTOR(S) : Sarvajit Chakravarty et al.

It is certified that error appears in the above-identified patent and that said Letters Patent is hereby corrected as shown below:

Drawings,
Replace formal drawings with the following.

Signed and Sealed this

Twenty-fourth Day of May, 2005

JON W. DUDAS
*Director of the United States Patent and Trademark Office*

Figures 1, 1B, 2:
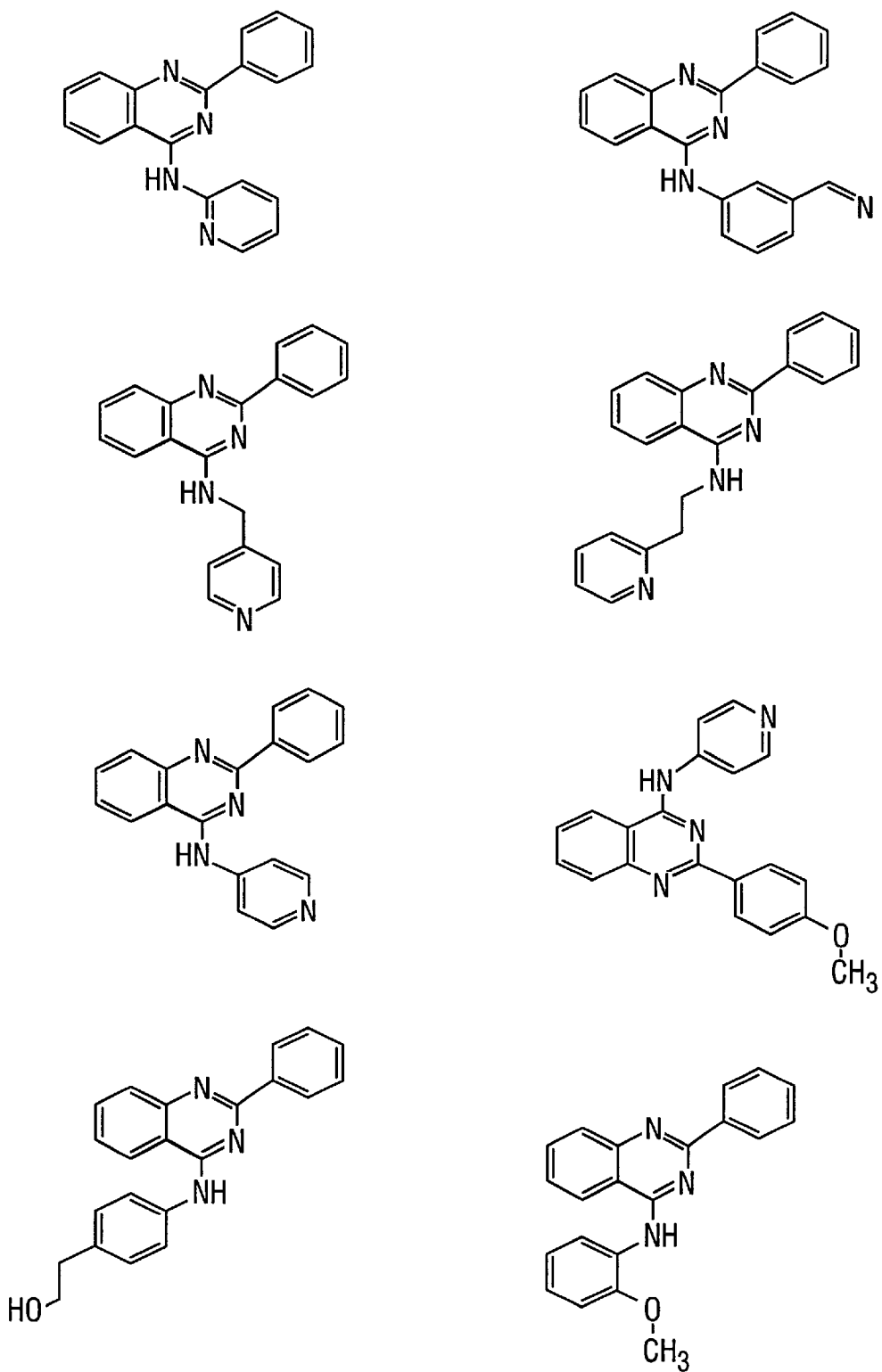
Figures 1, 1B, 2, 3:
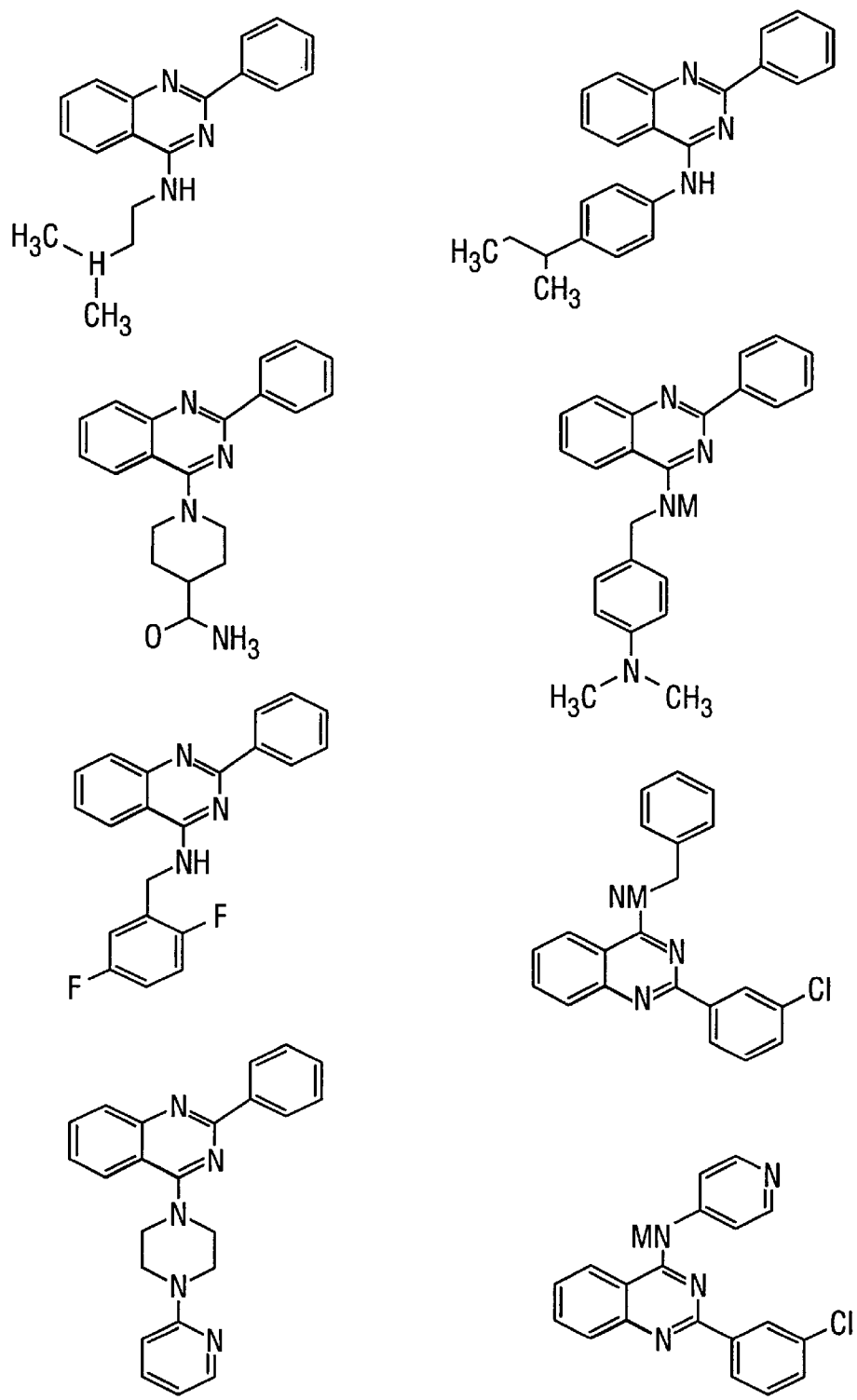
Figures 1, 1B, 2, 3, 4:
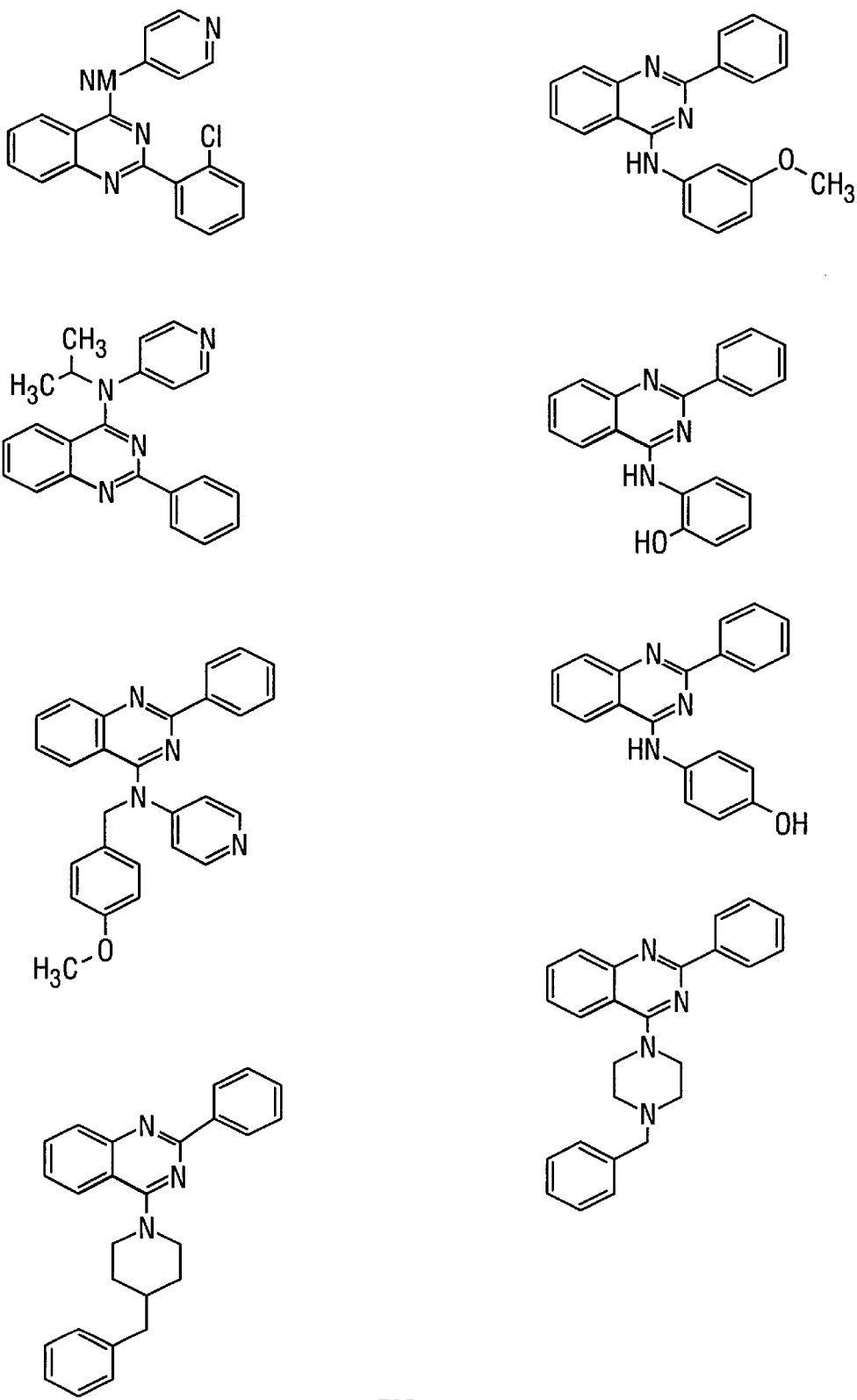
Figures 1, 1C, 2:
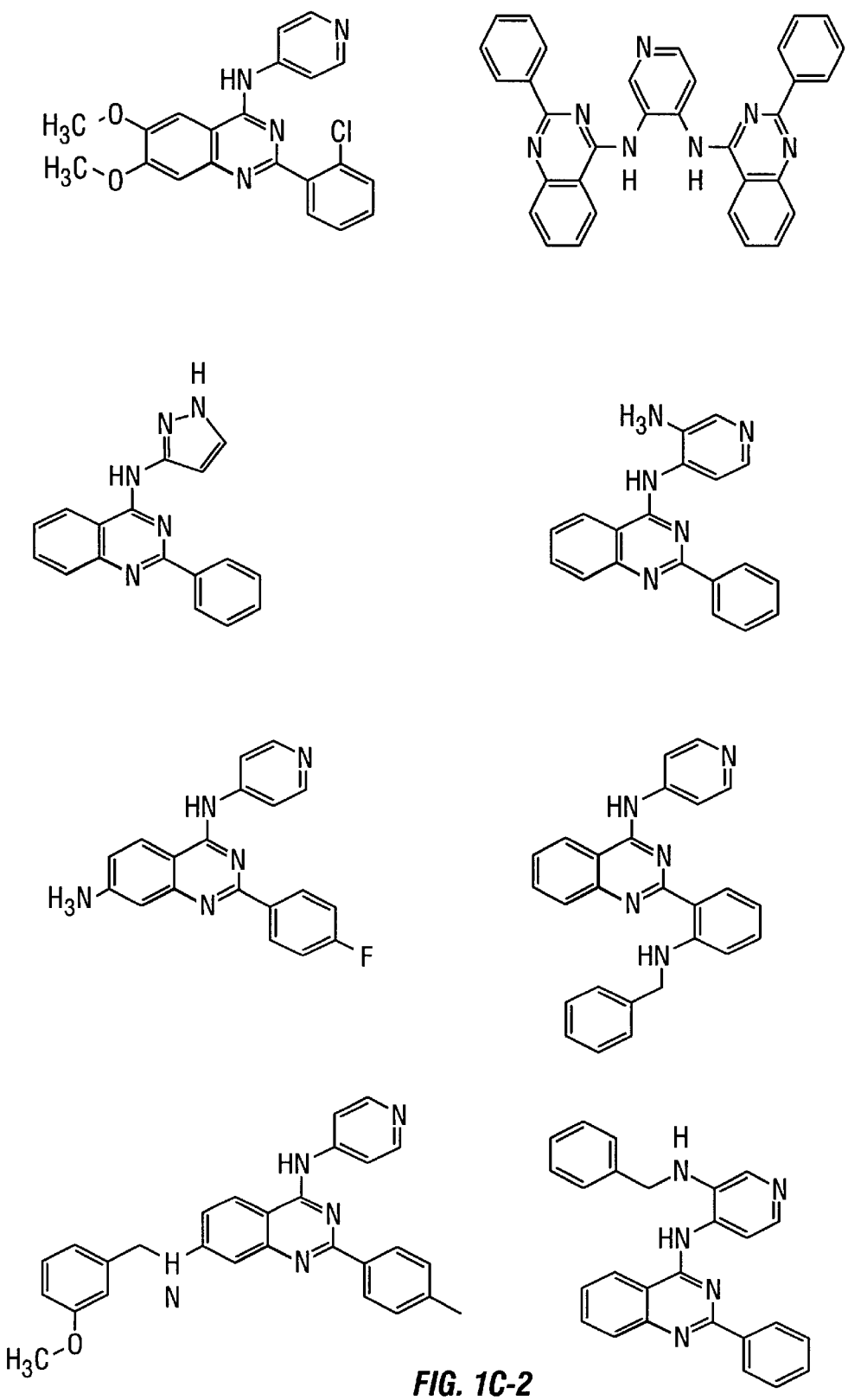
Figures 1, 1C, 2, 3:
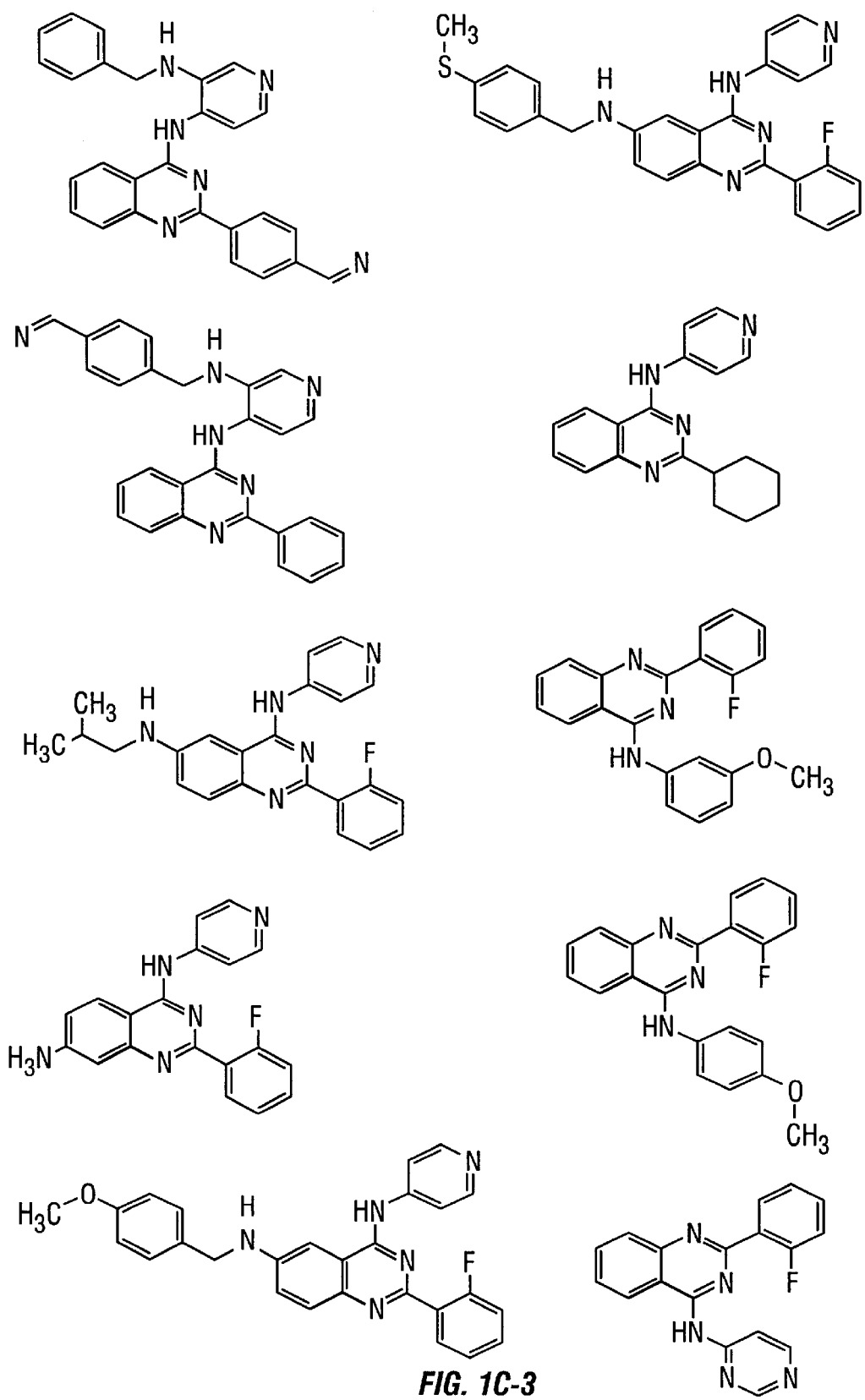
Figures 1, 1A:
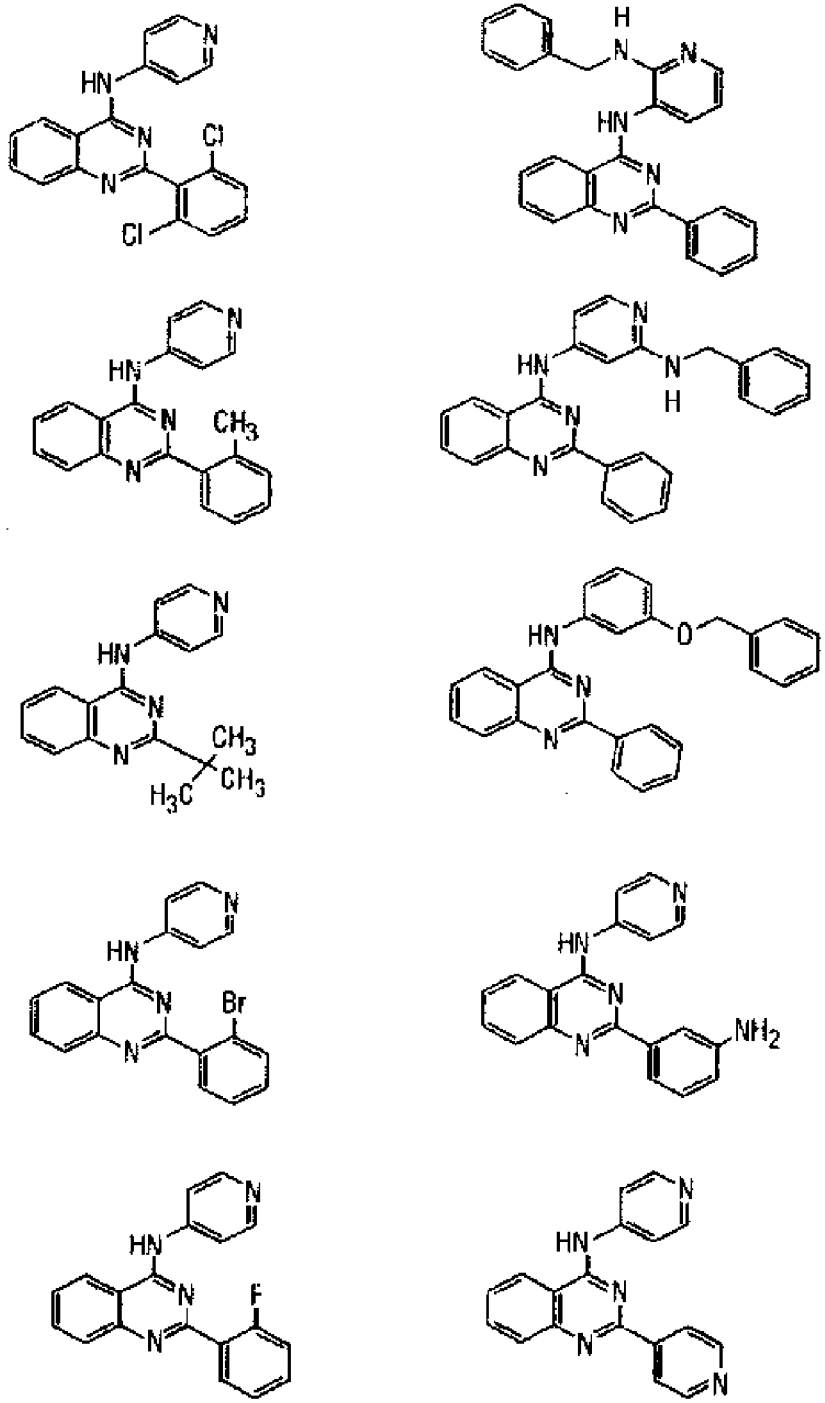
Figures 1, 1A, 2:
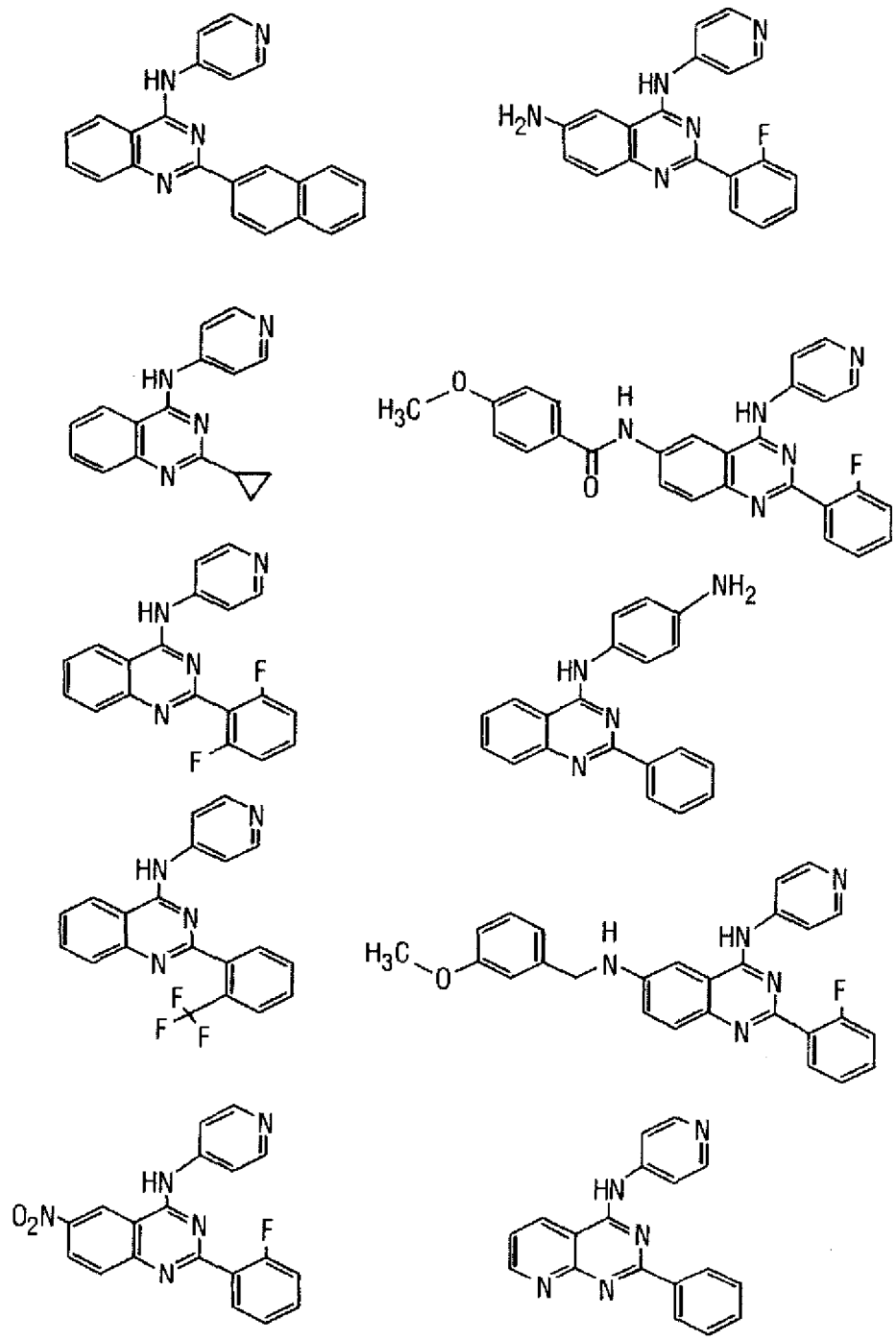
Figures 1, 1B, 2:
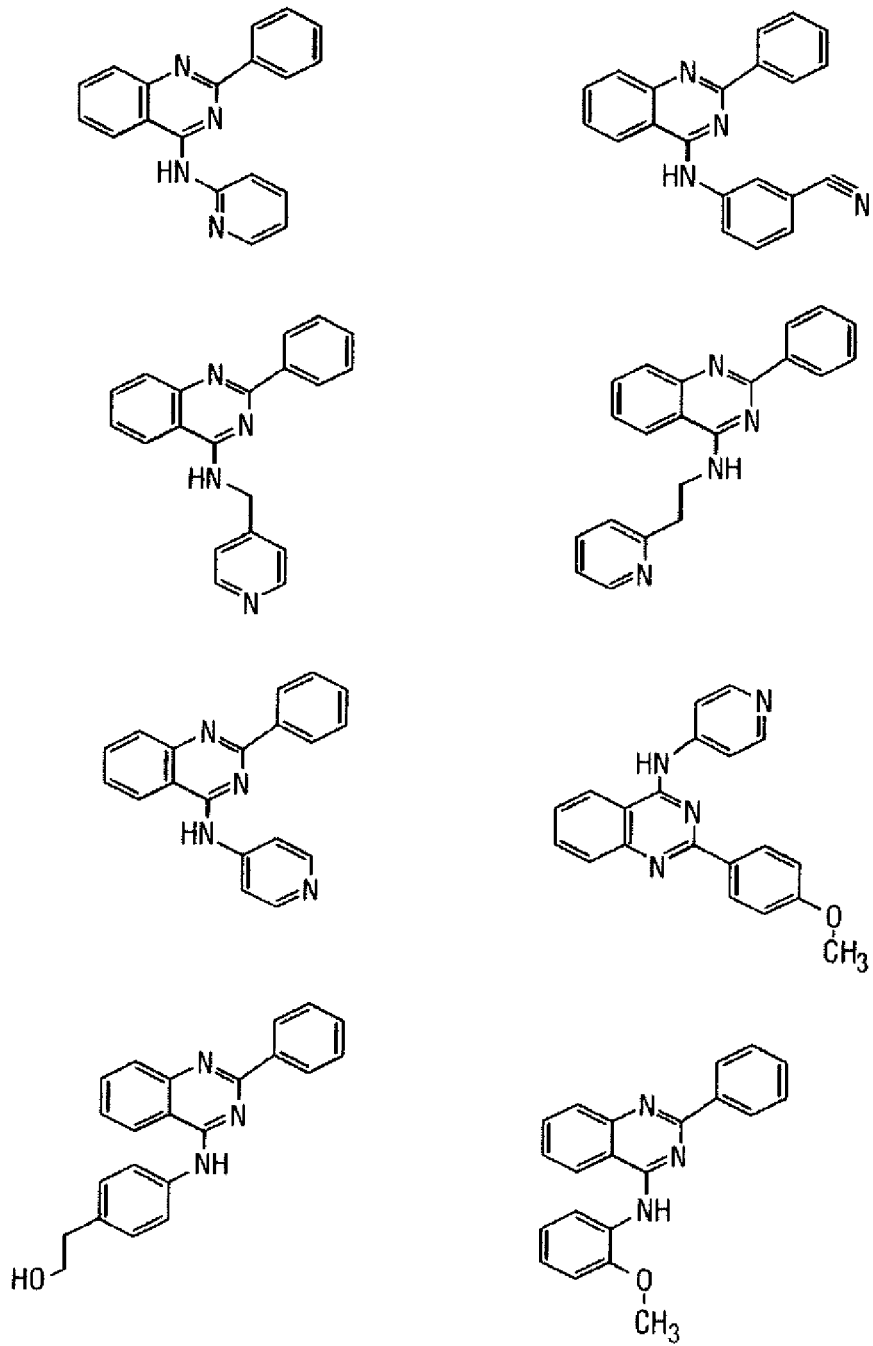
Figures 1, 1B, 2, 3:
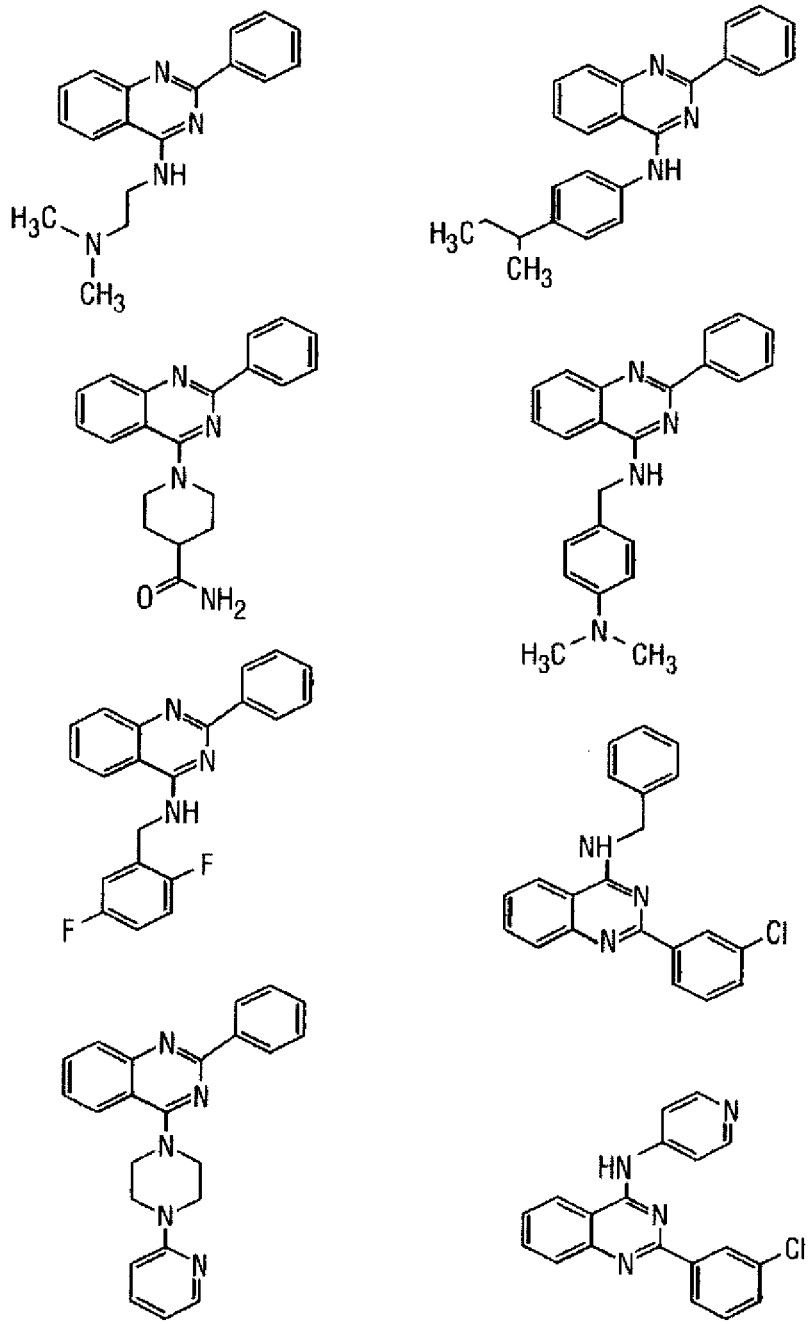
Figures 1, 1B, 2, 3, 4, 5:
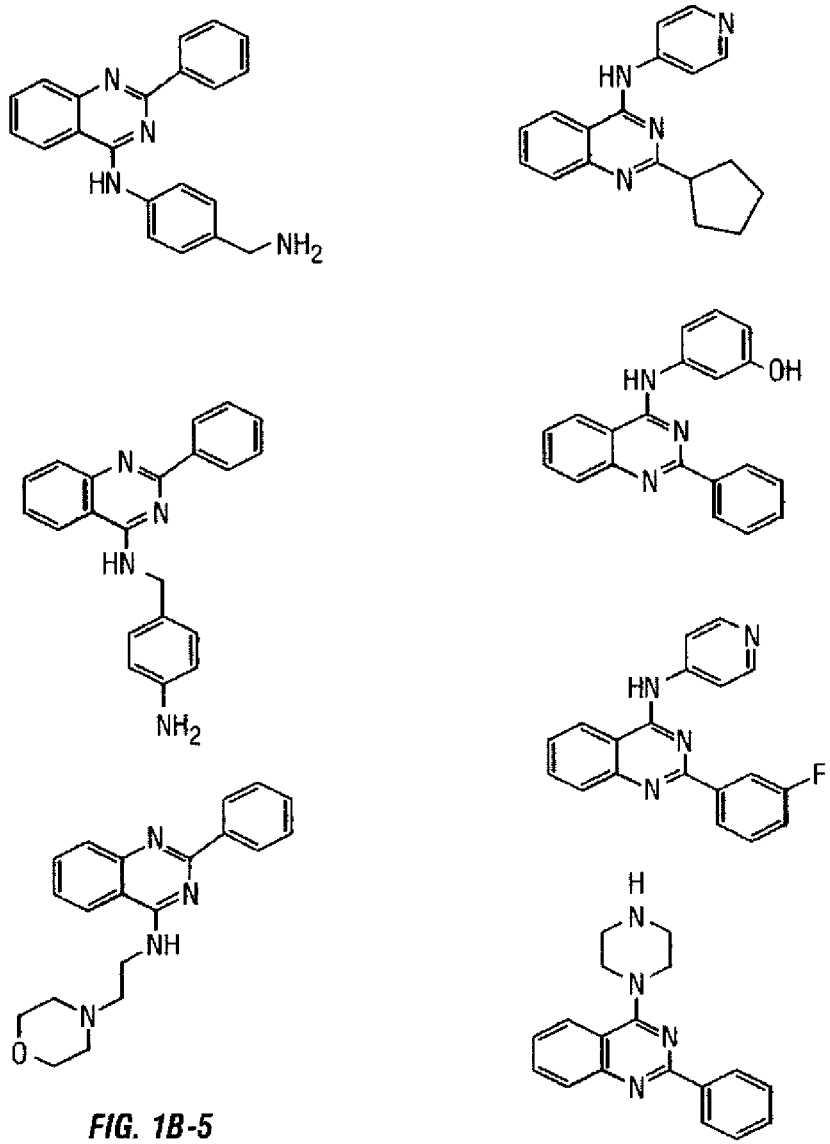
Figures 1, 1C:
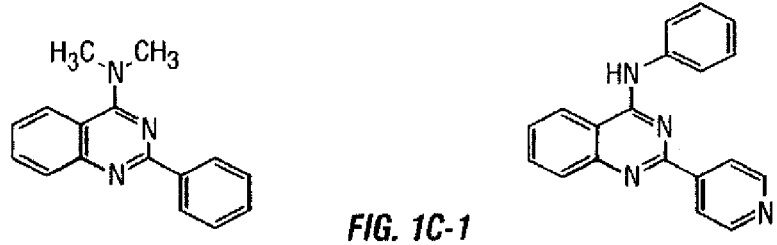
Figures 1, 1C, 2:
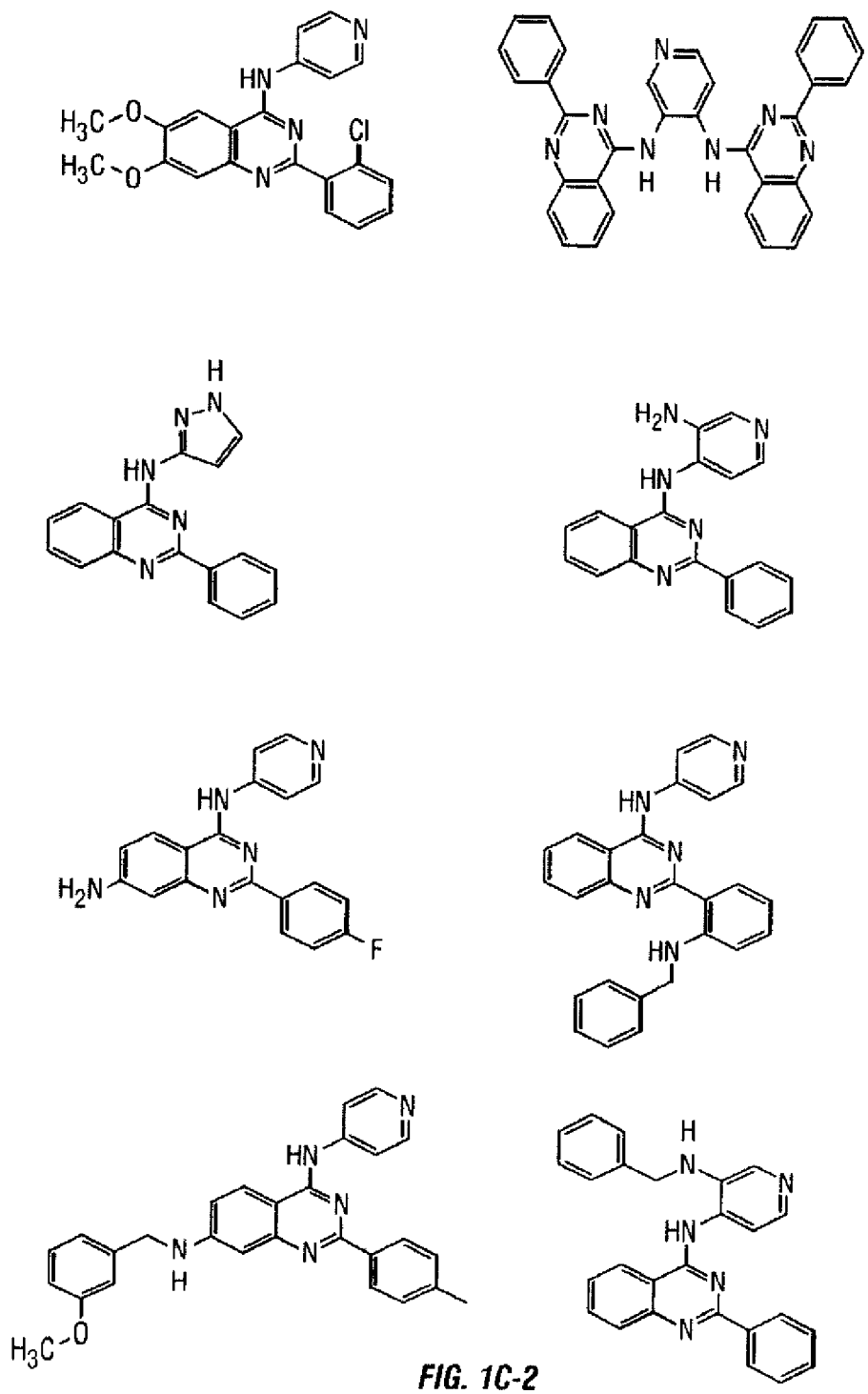
Figures 1, 1C, 2, 3:
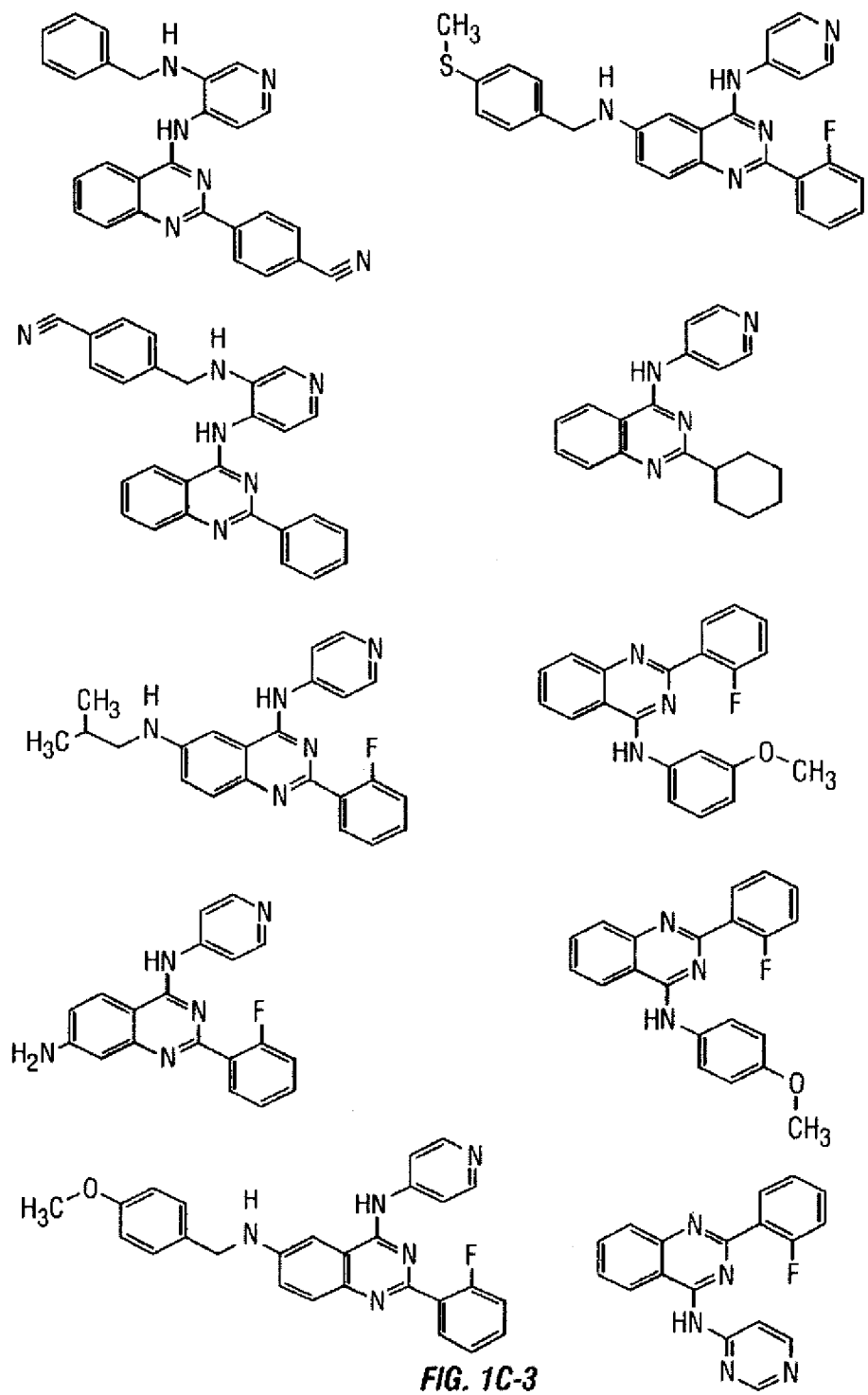

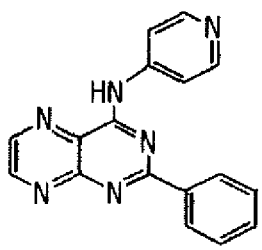
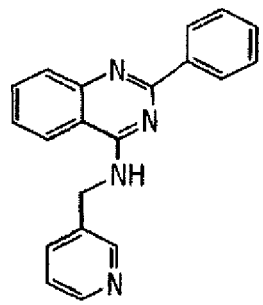
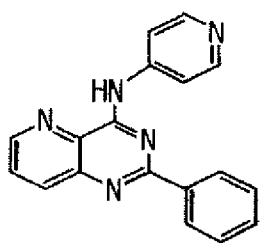
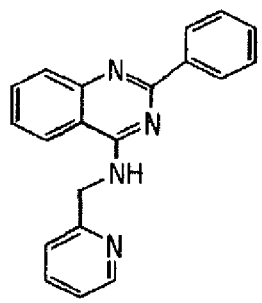
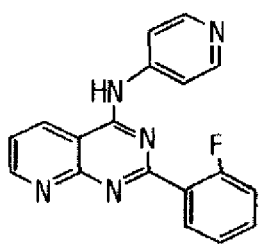
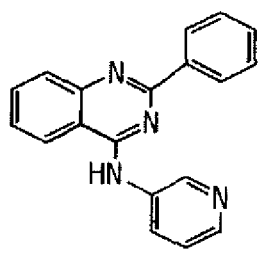
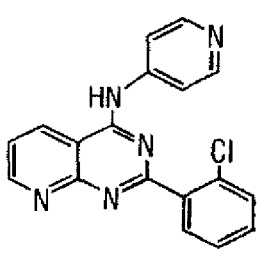
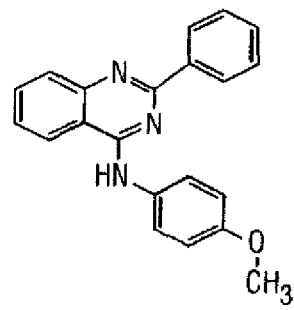
*FIG. 1A-3*
*FIG. 1B-1*

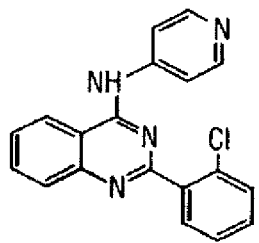
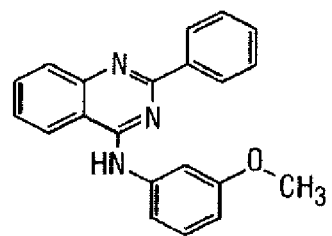
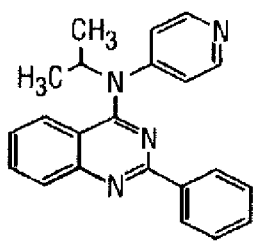
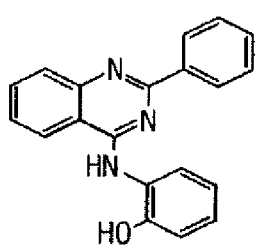
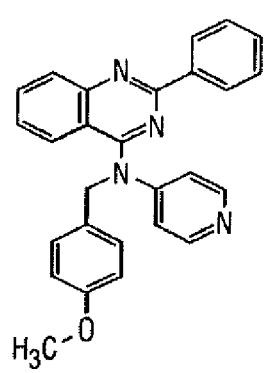
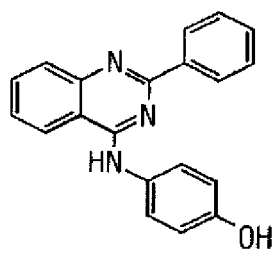
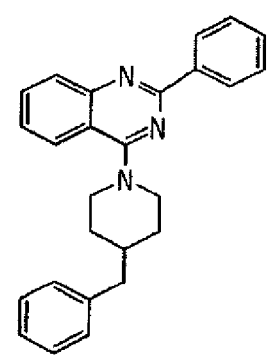
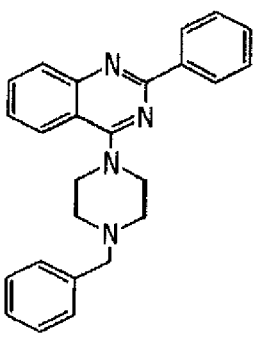
*FIG. 1B-4*

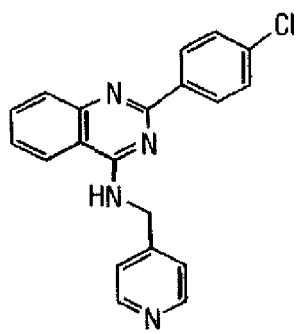
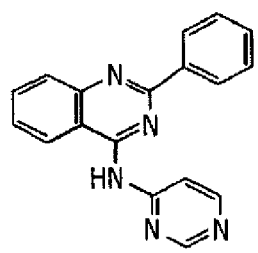
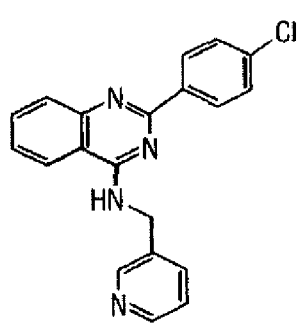
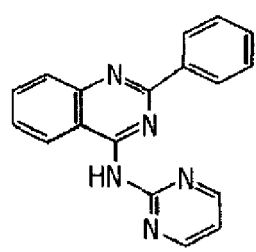
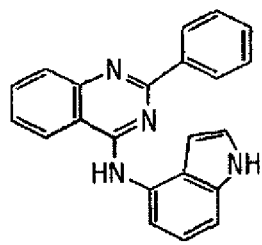
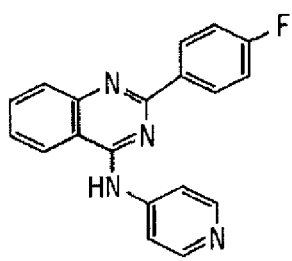
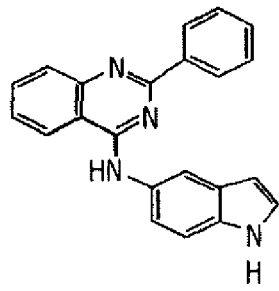
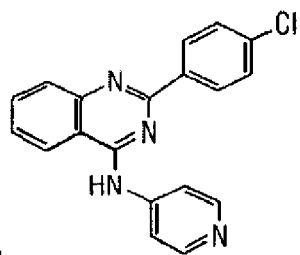
FIG. 1C-4